United States Patent
Ikeda et al.

(10) Patent No.: US 6,291,520 B1
(45) Date of Patent: Sep. 18, 2001

(54) HYDROXAMIC ACID AND N-HYDROXYUREA DERIVATIVES AND THEIR USE

(75) Inventors: Takafumi Ikeda; Akiyoshi Kawai; Takashi Mano, all of Handa; Yoshiyuki Okumura, Chita-gun; Rodney William Stevens, Handa, all of (JP)

(73) Assignee: Pfizer, New York, NY (US)

( * ) Notice: Subject to any disclaimer, the term of this patent is extended or adjusted under 35 U.S.C. 154(b) by 0 days.

(21) Appl. No.: 08/070,327

(22) PCT Filed: Nov. 13, 1991

(86) PCT No.: PCT/US91/08246

§ 371 Date: Jun. 28, 1993

§ 102(e) Date: Jun. 28, 1993

(87) PCT Pub. No.: WO92/09566

PCT Pub. Date: Jun. 11, 1992

(30) Foreign Application Priority Data

Nov. 27, 1990 (JP) .................................................... 2-323814

(51) Int. Cl.⁷ .......................... A61K 31/27; C07C 259/04
(52) U.S. Cl. ........................................... 514/486; 562/623
(58) Field of Search .............................. 562/623; 514/486

(56) References Cited

U.S. PATENT DOCUMENTS 5,187,192    2/1993    Brooks et al. ........................ 514/445

FOREIGN PATENT DOCUMENTS

| 0196184 | 10/1986 | (EP) . |
| 0292699 | 11/1988 | (EP) . |
| 0408760 | 1/1991 | (EP) . |
| 0436199 | 7/1991 | (EP) . |
| 9209567 | 6/1992 | (WO) . |

*Primary Examiner*—Deborah C. Lambkin
(74) *Attorney, Agent, or Firm*—Peter C. Richardson; Paul H. Ginsburg; Elsa Djuardi

(57) ABSTRACT

Certain novel hydroxamic acid derivatives having the structure

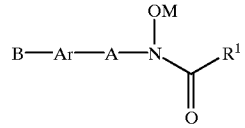

inhibit the enzyme lipoxygenase. These compounds, and the pharmaceutically acceptable salts thereof, are useful in the treatment or alleviation of inflammatory diseases, allergic conditions and cardiovascular diseases in mammals and as the active ingredient in pharmaceutical compositions for treating such conditions.

29 Claims, No Drawings

HYDROXAMIC ACID AND N-HYDROXYUREA DERIVATIVES AND THEIR USE

This application is a 371 of PCT/US91/08246 Nov. 13, 1991.

BACKGROUND OF THE INVENTION

1. Field of the Invention

This invention relates to novel hydroxamic acid and N-hydroxyurea derivatives. The compounds of the present invention inhibit the enzyme lipoxygenase, and are useful in the treatment or alleviation of inflammatory diseases, allergy and cardiovascular diseases in mammals. This invention also relates to pharmaceutical compositions comprising such compounds and to the use of such compounds in treating inflammatory diseases, allergy and cardiovascular diseases in mammals. This invention further relates to methods of making such compounds.

Arachindonic acid is known to be the biological precursor of several groups of endogenous metabolites, prostaglandins including prostacyclins, thromboxanes and leukotrienes. The first step of arachidonic acid metabolism is the release of arachidonic acid and related unsaturated fatty acids from membrane phospholipids, via the action of phospholipase. Free fatty acids are then metabolized either by cyclooxygenase to produce the prostaglandins and thromboxanes or by lipoxygenase to generate hydroperoxy fatty acids which may be further converted to the leukotrienes. Leukotrienes have been implicated in the pathophysiology of inflammatory diseases, including rheumatoid arthritis, gout, asthma, ischemia reperfusion injury, psoriasis and inflammatory bowel disease. Any drug that inhibits lipoxygenase is expected to provide significant new therapy for both acute and chronic inflammatory conditions.

2. Description of the Related Art

Recently several review articles on lipoxygenase inhibitors have been reported (See H. Masamune et al., *Ann. Rep. Med. Chem.*, 24, 71–80 (1989) and B. J. Fitzsimmons et al., *Leukotrienes and Lipoxygenases*, 427–502 (1989).

Compounds of the same general class as the compounds of the present invention are disclosed in EP 279263 A2, EP 196184 A2, JP 63502179 and U.S. Pat. No. 4,822,809.

SUMMARY OF THE INVENTION

The present invention provides novel hydroxamic acid and N-hydroxyurea derivatives of the formula

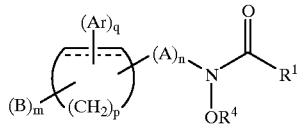

wherein n is 0 or 1; m is 0 to 3; p is 1 to 6; q is 1 or 2; $R^1$ is hydrogen, C1 to C4 alkyl, C2 to 4 alkenyl, alkylthioalkyl, alkoxyalkyl or $NR^2R^3$ wherein $R^2$ and $R^3$ are each independently hydrogen, C1 to C4 alkyl, hydroxy, aryl, or aryl substituted with one or more substituents selected from the group consisting of halo, nitro, cyano, C1 to C12 alkyl, C1 to C12 alkoxy, C1 to C12 halosubstituted alkyl, C1 to C12 hydroxysubstituted alkyl, C1 to C12 alkoxycarbonyl, aminocarbonyl, C1 to C12 alkylaminocarbonyl, di C1 to C12 alkylaminocarbonyl and C1 to C12 alkylsulfonyl, provided that $R^2$ and $R^3$ are not both hydroxy; $R^4$ is hydrogen, a pharmaceutically acceptable cation, aroyl, or C1 to C6 alkoyl; A is C1 to C6 alkylene or C2 to C6 alkenylene; each B is independently hydrogen, halo, nitro, cyano, SH hydroxy C1 to C6 alkyl, C1 to C6 halosubstituted alkyl, C2 to C6 alkenyl, C1 to C6 alkoxy, C1 to C6 thioalkyl, C1 to C12 aminocarbonyl, C1 to C6 alkylaminocarbonyl, di C1 to C6 alkylaminocarbonyl or C1 to C-2 alkoxyalkyl; each Ar is independently phenyl, naphthyl, pyridyl, quinolyl, thienyl, furyl or phenoxyphenyl or any of the foregoing substituted with one or more substituents selected from the group consisting of hydroxy, halo, nitro, cyano, —SH, C1 to C12 alkyl, C1 to C12 alkoxy, C1 to C12 halosubstituted alkyl, C1 to C12 hydroxysubstituted alkyl, C1 to C12 alkylamino, di C1 to C12 alkylamino, C1 to C12 alkoxycarbonyl, aminocarbonyl, C1 to C12 alkaminocarbonyl, di C1 to C12 alkylaminocarbonyl and C1 to C12 alkylsulfonyl. The groups Ar, B and the linking group a may be attached at any available position on the ring. Ar and B may be taken together, along with the carbon atoms to which they attached, to form a ring. The dotted line in the chemical formula represents an optional double bond.

This invention also concerns pharmaceutical compositions comprising a pharmaceutically acceptable carrier or diluent and a compound of the invention or a pharmaceutically acceptable salt thereof. This invention further concerns methods of treating inflammatory diseases, allergy and cardiovascular diseases in mammals comprising administration of such compounds or compositions.

DETAILED DESCRIPTION OF THE INVENTION

Definitions

As used herein, the following definitions are used.

"Halo" and "halogen" mean radicals derived from the elements fluorine, chlorine, bromine and iodine.

"Alkyl" means straight or branched saturated hydrocarbon radicals, for example, methyl, ethyl, n-propyl and isopropyl.

"Alkenyl" means straight or branched unsaturated (double bonded) hydrocarbon radicals, for example, ethenyl, 1- or 2-propenyl, 2-methyl-1-propenyl and 1- or 2-butenyl.

"Alkylene" means straight and branched saturated hydrocarbon radicals, for example, —CH$_2$—,- —CH(CH$_3$)—, —C(CH$_3$)$_2$—, —CH$_2$CH$_2$—, —CH$_2$CH(CH$_3$)—, —CH(C$_2$H$_5$)—, —C(CH$_3$)$_2$C(CH$_3$)$_2$— and —CH$_2$CH$_2$CH$_2$—.

"Alkenylene" means straight or branched unsaturated (double bonded) hydrocarbon radicals, for example, —CH═CH—, —CH═CHCH$_2$, —CH═CHCH(CH$_3$)—, —C(CH$_3$)═CHCH$_3$— and —CH$_2$CH═CHCH$_2$—.

"Alkoxy" means —OR$^5$ wherein R$^5$ is an alkyl radical, for example, methoxy, ethoxy, propoxy, isopropoxy and butoxy.

"Alkoxyalkyl" means —R$^6$OR$^7$ wherein R$^5$ and R$^7$ are independently alkyl radicals, for example, methoxymethyl, methoxyethyl, ethoxymethyl and ethoxyethyl.

"Thioalkyl" means —SR$^8$ wherein R$^8$ is an alkyl radical, for example, methylthio, ethylthio, propylthio and butylthio.

"Alkylamino" means —NHR$^9$ wherein R$^9$ is an alkyl radical, for example, methylamino, ethylamino, propylamino and butylamino.

"Dialkyamino" means —NR$^9$R$^{10}$ wherein R$^9$ and R$^{10}$ are alkyl radicals, for example, dimethylamino, methylethylamino and diethylamino.

"Alkylthioalkyl" means —R$^{11}$SR$^{12}$ wherein R$^{11}$ and R$^{12}$ are independently alkyl radicals, for example, methylthiomethyl, ethylthioethyl and methylthioethyl.

"Alkoyl" means —COR$^{13}$ wherein R$^{13}$ is an alkyl radical, for example, formyl, acetyl, propionyl, butyryl and isobutyryl.

"Aryl" means aromatic radicals, for example, phenyl, naphthyl, pyridyl, quinolyl, thienyl, furyl and phenoxyphenyl.

"Aroyl" means —COR$^{14}$ wherein R$^{14}$ is an aryl radical, for example, benzoyl and naphthoyl.

"Alkoxycarbonyl" means —C(=O)R$^{15}$ wherein R$^{15}$ is an alkoxy radical, for example, methoxycarbonyl, ethoxycarbonyl and propoxycarbonyl.

"Alkylaminocarbonyl" means —C(=O)NHR$^{16}$ wherein R$^{16}$ is an alkyl radical, for example, methylaminocarbonyl, ethylaminocarbonyl and propylaminocarbonyl.

"Dialkylaminocarbonyl" means —C(=O)NR$^{17}$R$^{16}$ wherein R$^{17}$ and R$^{18}$ are independently alkyl radicals, for example, dimethylaminocarbonyl, diethylaminocarbonyl and methylethylaminocarbonyl.

"Alkylsulfonyl" means —SO$_2$R$^{19}$ wherein R$^{19}$ is an alkyl radical, for example, methanesulfonyl (mesyl) and ethanesulfonyl.

"Halosubstituted alkyl" means an alkyl radical as described above substituted with one or more halogens, for example, chloromethyl, trifluoromethyl and 2,2,2-trichloroethyl.

"Hydroxysubstituted alkyl" means an alkyl radical as described above substituted with one or more hydroxy radicals, for example, hydroxymethyl, dihydroethyl and trihydroxypropyl.

"Pharmaceutically acceptable cation" means non-toxic cations based on alkali and alkaline earth metals, for example, sodium, lithium, potassium, calcium and magnesium, as well as non-toxic ammonium, quaternary ammonium, and amine cations, for example, ammonium, tetramethyl-ammonium, methylamine, dimethylamine, trimethylamine, ethylamine, diethylamine and triethylamine.

Methods of Preparation

The compounds of the invention may be prepared by a number of synthetic methods. See, for example, analogous procedures in JP application No. 105048/90. As used in the following reaction schemes, Q is

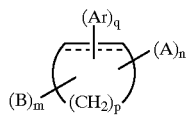

and A, B, Ar, m, n and p are as defined above. Although in Schemes 1 and 2, below, R$^1$ is methyl and NH$_2$, respectively, compounds wherein R$^1$ is otherwise, as defined above, may be prepared in a similar manner.

In one embodiment, compounds of formula III are prepared according to the reaction steps outlined in Scheme 1.

Reaction Scheme 1

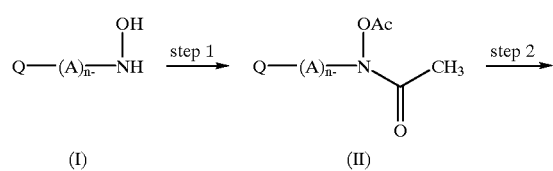

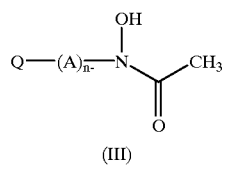

(III)

In step 1, the diacetyl compound (II) is prepared by standard methods known in the art. For example, the hydroxylamine (I) is reacted with acetyl chloride or acetic anhydride in a reaction-inert solvent in the presence of a suitable base, Preferred bases are sodium hydride, triethylamine and pyridine, with the latter two being particularly preferred. Suitable reaction-inert solvents include methylene chloride, chloroform, tetrahydrofuran, benzene and toluene. The reaction is usually carried out in the temperature range of about 0° C. through to ambient temperature, with reaction times from 30 minutes to a few hours being typical. The product can be isolated and purified by conventional procedures, such as recrystallization or chromatography.

Step 2 involves selective hydrolysis of the diacetyl (II) with an appropriate base. Typical bases include ammonium hydroxide, sodium hydroxide, potassium hydroxide and lithium hydroxide preferably in methanol, ethanol, isopropyl alcohol or water, through binary solvent systems such as alcohol-water, tetrahydrofuran-water and the like may also be employed. Reaction temperatures are usually in the range of about −10° C. through to ambient temperature, with the reaction usually complete with a few minutes to several hours. The product of formula III is isolated by standard methods and purification can be achieved by conventional means, such as recrystallization and chromatography.

In another embodiment, compounds of the formula IV are prepared as illustrated in Scheme 2.

Reaction Scheme 2

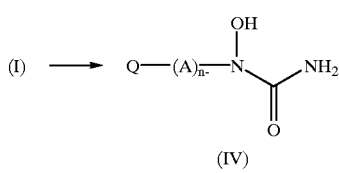

In this step the hydroxylamine (I) is treated with trimethylsilyl isocyanate in a reaction-inert solvent usually at ambient through to reflux temperature. Suitable solvents which do not react with reactants and/or products include, for example, tetrahydrofuran, dioxane, methylene chloride and benzene. An alternative procedure employs treatment of the hydroxylamine (I) with gaseous hydrogen chloride in a reaction-inert solvent such as benzene or toluene followed by treatment with phosgene. Reaction temperatures are usually in the range of ambient temperature through to boiling point of solvent. The intermediate carbamoyl chloride is not isolated but is subjected to (i.e. in situ) reaction with aqueous ammonia. The product of formula IV thus obtained is isolated by standard methods and purification can be achieved by conventional means, such as recrystallization and chromatography.

The aforementioned hydroxylamine (I) is easily prepared by standard synthetic procedures from readily available carbonyl compounds, for example, ketones, aldehydes, alcohols and halogen compounds. See, for example, R. L. Danheiser et al., *Tetrahedron Lett.*, 28, 3299 (1987), M.

Kolobielski et al., *J. Am. Chem. Soc.,* 79, 5820 (1957), Y. Kobayashi et al., *J. Org. Chem.,* 47, 3232 (1982) and Fieser et al., *J. Am. Chem. Soc.,* 70, 3147 (1948). For example, a suitable carbonyl compound is converted to its oxime and is then reduced to the requisite hydroxylamine (I) with a suitable reducing agent. See, for example, R. F. Borche et al., *J. Am. Chem. Soc.,* 93, 2897 (1971). Preferred reducing agents include sodium cyanoborohydride and borane-complexes such as boron-pyridine, boron-triethylamine and boron-dimethylsulfide; triethylsilane in trifluoroacetic acid may also be employed.

Alternatively, the hydroxylamine (I) can be prepared by treating the corresponding alcohol with N,O-bis(tert-butyloxycarbonyl)hydroxylamine under Mitsunobu-type reaction conditions followed by acid catalyzed hydrolysis of the N,O-protected intermediate product (see JP 1045344). It is also noteworthy that the N,O-diacetyl compound (II) can be prepared employing N,O-diacetylhydroxylamine in place of N,O-bis(tert-butyloxycarbonyl) hydroxylamine, thus providing a convenient route to the product of formula III.

The aforementioned hydroxylamine (I) may also be prepared from a suitable halide compound by reaction with an O-protected hydroxylamine and subsequent deprotection. See W. P. Jackson et al., *J. Med. Chem.,* 31, 499 (1988). Preferred O-protected hydroxylamines include O-tetrahydro-pyranyl-, O-trimethylsilyl- and O-benzylhydroxylamine.

The hydroxylamine of formula I thus obtained by the abovementioned representative procedures is isolated by standard methods and purification can be achieved by conventional means, such as recrystallization and chromatography.

The pharmaceutically acceptable salts of the novel compounds of the present invention are readily prepared by contacting said compounds with a stoichiometric amount of, in the case of a non-toxic cation, an appropriate metal hydroxide or alkoxide or amine in either aqueous solution or a suitable organic solvent. In the case of non-toxic acid salt, an appropriate mineral or organic acid in either aqueous solution or a suitable organic solvent can be used. The salt may then be obtained by precipitation or by evaporation of the solvent.

Biological Activity

The compounds of this invention inhibit lipoxygenase. This inhibition has been demonstrated by an assay using rat peritoneal cavity resident cells which determines the effect of such compounds on the metabolism of arachidonic acid.

The compounds of Examples 1 to 14 were tested according to the methods described in "synthesis in leukotrienes by peritoneal macrophages", *Jap. J. Inflammation,* 7, 145–150 (1987), and were shown to be lipoxygenase inhibitors. In this test some preferred compounds exhibit low $IC_{50}$ values, in the range of about 0.5 to about 30 $\mu$M, for lipoxygenase inhibition.

The ability of the compounds of the present invention to inhibit lipoxygenase makes them useful for controlling the symptoms induced by the endogenous metabolites arising from arachidonic acid in a mammalian subject. The compounds are therefore valuable in the prevention and treatment of such disease states in which the accumulation of arachidonic acid metabolites is the causative factor, e.g., allergic bronchial asthma, skin disorders, rheumatoid arthritis, osteoarthritis and thrombosis.

The compounds of the formula and their pharmaceutically acceptable salts are of particular use in the prevention and treatment of inflammatory diseases, allergy and cardiovascular diseases in a human subject.

Methods of Administration

For treatments of the various conditions described above, the compounds of the invention and their pharmaceutically acceptable salts can be administered to a human subject either alone or, preferably, in combination with pharmaceutically acceptable carriers or diluents in a pharmaceutical composition, according to standard pharmaceutical practice. A compound can be administered via a variety of conventional routes of administration including orally, parenterally and by inhalation. When the compounds are administered orally, the dose range will generally be from about 0.1 to about 20 mg/kg/day, based on the body weight of the subject to be treated preferably from about 0.1 to about 1.0 mg/kg/day in single or divided doses. If parenteral administration is desired, then an effective dose will generally be from about 0.1 to about 1.0 mg/kg/day. In some instances it may be necessary to use dosages outside these limits, since the dosage will necessarily vary according to the age, weight and response of the individual patient as well as the severity of the patient's symptoms and the potency of the particular compound being administered.

For oral administration the compounds of the invention and their pharmaceutically acceptable salts can be administered, for example, in the form of tablets, powders, lozenges, syrups or capsules, or as an aqueous solution or suspension. In the case of tablets for oral use, carriers which are commonly used include lactose and corn starch. Lubricating agents, such as magnesium stearate, are commonly added. In the case of capsules, useful diluents are lactose and dried corn starch. When aqueous suspensions are required for oral use, the active ingredient is combined with emulsifying and suspending agents. If desired, certain sweetening and/or flavoring agents can be added.

For intramuscular, intraperitoneal, subcutaneous and intravenous use, a sterile solution of the active ingredient is usually prepared, and the pH of the solutions should be suitably adjusted and buffered. For intravenous use, the total concentration of solute should be controlled to make the preparation isotonic.

Examples

The present invention is illustrated by the following examples. However, it should be understood that the invention is not limited to specific details of these examples. Proton nuclear magnetic resonance (NMR) spectra were measured at 270 MHz unless otherwise indicated and peak positions are expressed in parts per million (ppm) downfield from tetramethylsilane. The peak shapes are denoted as follows: s, singlet; d, doublet; t, triplet; q, quartet; m, multiplet; br, broad.

Example 1

N-Hydroxy-N-[(trans-2-phenyl-1-cyclopropyl)methyl]urea

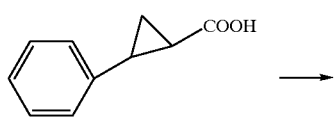

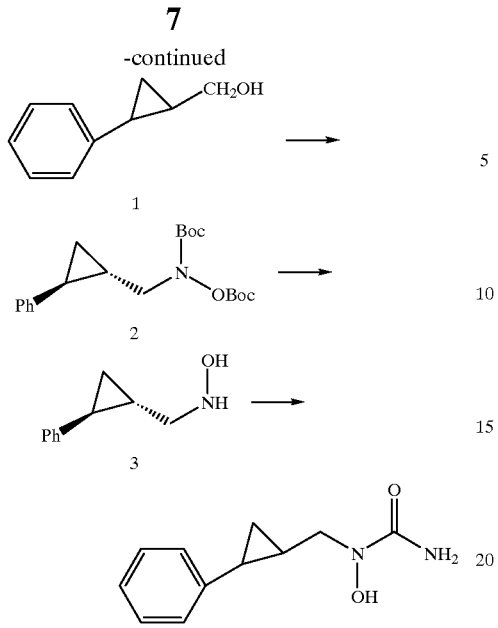

Step 1, trans-2-phenyl-1-cyclopropyl methanol

To a cooled stirred solution of 2-phenylcyclopropanecarboxylic acid (1.62 g, 10 mmol) in THF (80 ml) was added sodium borohydride (567 mg, 15 mmol) at 0° C. To this mixture was added dropwise boron trifluoride etherate (2.13 g, 15 mmol) and the reaction mixture was stirred for 1 hour at 0° C., then stirred overnight at room temperature. The mixture was diluted carefully with water and extracted with EtOAc (200 ml). The EtOAc layer was washed with water (70 ml) and brine (80 ml). The solution was dried over MgSO₄ and concentrated in vacuo, affording 1.49 g (100% yield) of product (1) as a colorless oil.

IR (neat) v 3350, 1605, 1490, 1090, 1035, 1020, 695 cm$^{-1}$.

$^1$H NMR (CDCl₃) δ 7.05–7.29 (m, 5H), 3.62 (d, J=7 Hz, 2H), 2.28 (br s, 1H), 1.81 (m, 1H), 1.46 (m, 1H), 0.95 (m, 2H).

Step 2, N,O-bis(tert-butoxycarbonyl)-trans-2-phenyl-1-cyclopropylmethyl hydroxylamine To a cooled (−75° C.), stirred solution of the product of Step 1, above, (1.5 g, 10 mmol), N,O-bis-(tert-butoxycarbonyl)hydroxylamine (2.563 g, 11 mmol) and triphenylphosphine (3.93 g, 15 mmol) in dry toluene (35 ml) was added dropwise diethyl azodicarboxylate (2.612 g, 15 mmol) in dry toluene (10 ml) at −75° C. under N₂ atmosphere. The mixture was then warmed to room temperature, stirred for 1 hour and the volatiles were removed. Chromatographic purification of the residue (SiO₂, 100 g, eluted with EtOAc-n-hexane (1:5)) afforded 3.24 g (89.3% yield) of product (2) as a pale yellow oil.

$^1$H NMR (TMS/CDCl₃) δ 7.05–7.26 (m, 5H), 3.62 (m, 2H), 1.85 (m, 1H), 1.50 (m, 1H), 1.46 (s, 9H), 1.48 (s, 9H), 0.97 (m, 2H).

Step 3, trans-2-phenyl-1-cyclopropylmethylhydroxylamine

To a stirred solution of the product of Step 2, above, (3.16 g, 8.71 mmol) in CH₂Cl₂ (85 ml) was added trifluoroacetic acid (22 ml) and the reaction mixture was stirred overnight (18 hours) at room temperature. The volatiles were removed under reduced pressure and EtOAc (200 ml) was added. The organic layer was washed with water (50 ml), saturated NaHCO₃ solution, water (50 ml) and brine (50 ml). The solution was dried over MgSO₄, concentrated in vacuo and the resultant oil was purified on silica gel (150 g, CHCl₃-EtOH (40:1), affording 932 mg (65.6% yield) of product (3) as a colorless oil.

IR (neat) v 3250, 3050, 1605, 1495, 1455, 1300, 1090, 1030, 755 cm$^{-1}$.

$^1$H NMR (CDCl₃) δ 7.04–7.27 (m, 5H), 2.90 (dd, J=1.1, 6.9 Hz, 2H), 1.77 (m, 1H), 1.34 (m, 1H), 0.94 (m, 2H).

Step 4, N-Hydroxy-N-[(trans-2-phenyl-1-cyclopropyl)methyl]urea

To a stirred solution of the product of Step 3, above, (906 mg, 5.56 mmol) in THF (20 ml) was added trimethylsilyl isocyante (961 mg, 8.34 mmol) at room temperature. The reaction mixture was stirred for 1.5 hours, the volatiles were removed in vacuo and the resulting colorless solid was triturated with n-hexane, yielding 756 mg (65.9% yield) of the title compound as colorless crystals, m.p. 145.5–147.5° C.

IR (nujol) v 1610, 1560, 1145, 1090, 750, 690 cm$^{-1}$.

$^1$H NMR (CDCl₃) δ 9.24 (s, 1H), 7.0–7.3 (m, 5H), 5.55 (s, 2H), 3.60 (dd, J=7.4, 15 Hz, 1H), 3.45 (dd, J=7.4, 15 Hz, 1H), 1.92 (m, 1H), 1.50 (m, 1H), 0.95 (m, 2H).

Example 2

N-hydroxy-N-([(trans-2-(3-phenoxyphenyl)-1-cyclopropyl]methyl)urea

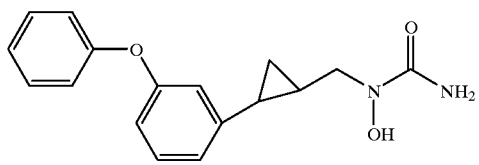

The compound of Example 2 was prepared according to the procedure of Example 1, using appropriate starting materials, yielding the title compound as an oil.

IR (neat) v 3200, 1650, 1580, 1450, 1415, 1250, 1220, 1165, 1150, 760 cm$^{-1}$.

$^1$H NMR (CDCl₃) δ 7.66 (s, 1H), 7.05–7.34 (m, 4H), 6.98 (m, 2H), 6.78 (m, 3H), 5.31 (s, 2H), 3.57 (dd, J=7.3, 14.7 Hz, 1H), 3.42 (dd, J=7.3, 14.7 Hz, 1H), 1.84 (m, 1H), 1.42 (m, 1H), 0.94 (m, 2H).

Example 3

N-hydroxy-N-([trans-2-(3-phenoxyphenyl)-1-cyclopropyl]methyl)acetamide

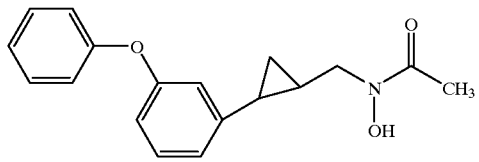

The compound of Example 3 was prepared according to the procedure of Example 1, using appropriate starting materials, yielding the title compound as an oil.

IR (neat) v 3160, 2900, 1610, 1580, 1490, 1250, 1220 cm$^{-1}$.

$^1$H NMR (CDCl$_3$) δ 8.38 (br s, 1H), 6.97–7.36 (m, 6H), 6.79 (m, 3H), 3.65 (m, 2H), 2.13 (s, 3H), 1.87 (m, 1H), 1.42 (m, 1H), 1.00 (m, 2H).

Example 4

N-[(2,2-difluoro-trans-3-phenyl-1-cyclopropyl)methyl]-N-hydroxyurea

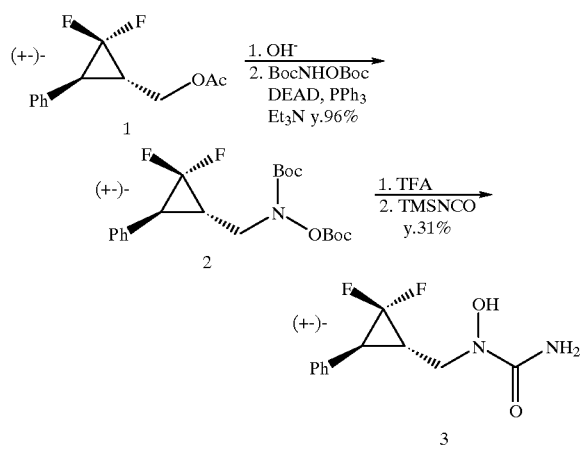

Step 1, N,O-di-tert-butoxycarbonyl-N-[(2,2-difluro-trans-3-phenyl-1cyclopropyl)methyl]hydroxylamine A solution of KOH (2.60 g, 40 mmol) and (2,2-difluro-trans-3-phenyl-1-cyclopropyl)methyl acetate (4.52 g, 20 mmol, prepared according to the method of Y. Kobayashi et al., J. Org. Chem., 47, 3232 (1982)) in a mixture of methanol (20 ml), tetrahydrofuran (20) and water (50 ml) was stirred for 14 hours at room temperature. The reaction mixture was neutralized with 1N HCl and extracted with ether (100 ml, 2×50 ml). The combined organic phases were washed with saturated sodium bicarbonate (2×50 ml) and brine (50 ml), and dried over magnesium sulfae. Evaporation of the soluent gave the (2,2-difuloro-trans-3-phenyl-1-cyclopropyl) methanol with a quantitative yield.

To a stirred solution of the alcohol prepared in the preceding paragraph (3.30, 18.4 mmol), N,O-di-tert-butoxycarbonylhydroxylamine (5.36 g, 23.0 mmol) and triphenylphosphine (6.03 g, 23.0 mmol) in tolune (40 ml) was added dropwise a solution of diethyl azodicarboxylate (4.01 g, 23.0 mmol) in tolune (5 ml) over 20 minutes at –78° C. under a nitrogen atmosphere. After stirring for 30 minutes, the cooling bath was removed and the reaction mixture was stirred for 4 hours at room temperature. The precipitates were filtered off and the filtrate was concentrated under reduced pressure. The residue was purified by column chromatography on silica gel (300 g) using 10% ethyl acetate in n-hexane as an eluent to give 7.03 g (17.6 mmol, 96% yield) of the title compound, which was solidifed on standing, m.p. 62–64° C.

IR (KBr) v 1782, 1724 cm$^{-1}$.

$^1$H NMR (CDCl$_3$) δ7.36-7.21 (m, 5H), 3.99 (ddd, J=2.20, 7.70, 15.02 Hz, 1H), 3.79 (dd, J=7.70, 15.02 Hz, 1H), 2.62 (dd, J=7.70, 14.65 Hz, 1H), 2.21 (dq, J=7.70, 14.65 Hz, 1H), 1.49 (s, 9H), 1.48 (s, 9H).

Step 2, N-[(2,2-difluro-trans-3phenyl-1-cyclopropyl) methyl]-N-hydroxyurea

To a solution of the hydroxylamine prepared in Step 1, above, (7.03 g, 17.6 mmol) in dichloromethanie (50 ml) was slowly added trifluoracetic acid (13.6 ml) at 0° C. under stirring. After stirring for 13.5 hours at 0° C. to room temperature, the soluent was evaporated off. The residue was added to saturated sodium bicarbonate (50 ml) and extracted with ethyl acetate (2×100 ml). The combined extracts were washed with saturated sodium bicarbonate (50 ml) and brine (50 ml), and dried over magnesium sulfate. Evaporation of the solvent gave 3.02 g of crude N-[(2,2-difluro-trans-3-phenyl-1-cyclopropyl)methyl]hydroxylamine.

To a stirred solution of the hydroxylamine obtained as described in the above paragraph, in tetrahydrofuran (50 ml), was added trimethysilyl-isocyanate (85%, 3.08 g, 22.7 mmol), and the reaction mixture was stirred at room temperature for 4 hours. To the stirred reaction mixture was added methanol (30 ml) and 10 minutes later the solvent was evaoprated off. Trituration of the results with a mixture of isopropyl ether and n-hexane gave 2.41 g of solids. Recrystallization from 10% ethanol in isopropyl ether afforded 1.34 g (5.5 mmol), 31% yield) of the title compound, m.p. 139–140° C.

IR )KBr) v 3460, 3350, 3200, 1604, 1584 cm$^{-1}$.

$^1$H NMR (DMSO-d$_6$) δ9.52 (s, 1H), 7.38-7.24 (m, 5H) 6.44 (s, 2H), 3.75 (ddd, J=2.56, 7.70, 14.65 Hz, 1H), 3.53 (dd,J=7.70, 14.65 Hz, 1H), 2.85 (dd,J=7.70, 14.65 Hz, 1H), 2.28 (dq,J=7.70, 14.65 Hz,) 1H).

Anal. Calc. for C$_{11}$H$_{12}$F$_2$N$_2$O$_2$: C, 54.54; H, 4.90; N, 11.56. Found: C, 57.78; H, 5.11; N, 11.59.

Example 5

N-hydroxy-N-(cis-4-phenylcyclohexan-1-yl)urea

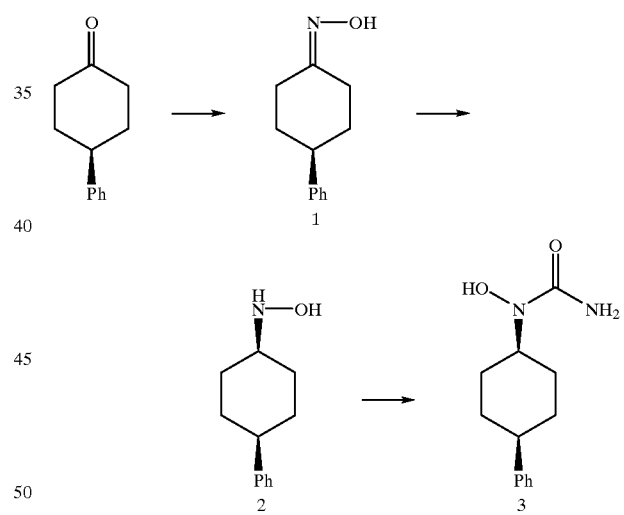

Step 1

4-Phencyclohexanone (5.00 g, 29 mmol) and hydroxylamine hydrochloride (5.20 g, 75 mmol) were dissolved in a mixture of methanol (40 ml) and pyridine (10 ml) and stirred overnight at ambient temperatue. The reaction mixture was concentrated in vacuo and the resultant residue was diluted with 1N HCl (100 ml) and extracted three times with ethyl acetate. The combined organic layers were dried over MgSO$_4$ and concentrated in vacuo to give 5.97 g (quantitative yield) of oxime (1) as white needles.

Step 2

The oxime prepared in Step 1, above, (5.45 g, 28.8 mmol) was dissolved in acetic acid (20 ml) and sodium cyanoborohydride (5.66 g, 90 mmol) was added portionwise over 1 hour. After reaction was complete, the reaction mixture was poured carefully into ice cold aqeous $K_2CO_3$ such that the pH was adjusted to 9. The mixture was extracted with ethyl acetate, dried over $MgSO_4$ and concentrated in vacuo to afford a diastereomeric mixture of hydroxylamines. Seperation on silica gel using 10% diisopropyl ether in hexane afforded 1.61 g (29% yield) of cis-hydroxylmaine (2, Rf=0.4) and 2.7 g (49% yield) of the trans isomer (Rf=0.2), both as white crystals.

$^1$H NMR (CDCl$_3$, cis isomer) δ 7.36-7.14 (m, 5H), 3.30-3.19 (m, 1H), 2.65-2.48 (m, 1H), 2.00-1.91 (m, 1H), 1.83-1.55 (m, 6H).

$^1$H NMR (CDCl$_3$, trans isomer) δ 7.35-7.14 (m, 5H), 2.98-2.87 (m, 1H), 2.57-2.45 (m, 1H), 2.16-1.88 (m,4H), 1.63-1.42 (m, 2H), 1.34-1.16 (m, 2H).

Step 3, N-hydroxy-N (cis-4-phenylcyclohexan-1-yl) urea

The cis-hydroxylamine (1.43 g, 7.5 mmol) prepared in Step 2, above, was stirred for 1 hour with trimethylsilyl isocyanate (2.19 g, 19 mmol) in 20 ml of tetrahydrofuran. The reaction mixture was concentrated in vacauo and the residue recrystallized from ethyl acetate to give 0.452 g (26% yield) of title product as a fine white powder, m.p. 161.4–162.2° C.

IR (DBr) v 3500, 3200, 2950, 1660, 1630, 1560, 1490, 1440, 1160 cm$^{-1}$.

$^1$H NMR (DMSO-d$_6$) δ 8.87 (s, 1H), 7.48-7.30 (m, 4H), 7.22-7.10 (m,1H), 6.18 (s, 2H), 4.07-3.92 (m, 1H), 2.86-2.77 (m, 1H), 2.25-2.09 (m, 2H), 1.79-1.62 (m, 4H), 1.56-1.41 (m, 2H).

The compounds of Examples 6 to 10, below, were prepared according to analogous procedures.

Example 6

N-hydroxy-N-(trans-4-phenylcyclohexan-1-yl)ure

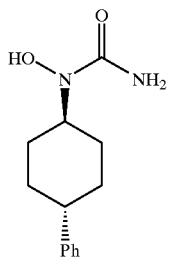

m.p. 161.9–162.6° C.

IR (KBr) v 3300, 3100, 2920, 2860, 1680, 1630, 1570, 1470, 1450, 1160 cm$^{-1}$.

$^1$H NMR (DMSO-d$_6$) δ 8.94 (s, 1H), 7.36-7.13 (m, 5H). 6.24 (s, 2H), 4.03-3.83 (m, 1H), 2.53-2.36 (m, 1H), 1.89-1.76 (m, 2H), 1.73-1.41 (m, 6H).

Example 7

N-hydroxy-N-cis-3-phenylcylohexan1-yl)urea

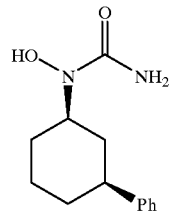

m.p. 144.1–144.9° C.

IR (DBr) v 3450, 3300, 2910, 1655, 1640, 1460, 1440 cm$^{-1}$.

$^1$H NMR (DMSO-d$_6$) δ 8.92 (s, 1H), 7.36-7.10 (m, 5H), 6.24 (s, 2H), 4.08-3.90 (m, 1H), 2.68-2.50 (m, 1lH), 1.92-1.25 (m, 8H).

Example 8

N-hydroxy-N-(trans-3-phenylcyclohexan-1-yl)urea

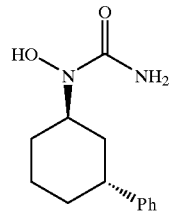

m.p. 132.9–133.7° C.

IR (KBr) v 3500, 3370, 2940, 2879, 1630, 1560, 1450, 1160 cm$^{-1}$.

$^1$H NMR (DMSO-d$_6$) δ 9.00 (s, 1H), 7.38-7.25 (m, 4H), 7.20-7.11 (m, 1H), 6.24 (s, 2H), 4.19-4.05 (m, 1H), 3.26-3.15 (m, 1H), 1.99-1.83 (m, 3H), 1.75-1.46 (m, 4H), 1.44-1.26 (m, 1H).

Example 9

N-hyroxy-N-(cis-2-phenylcyclohexan-1-yl)urea

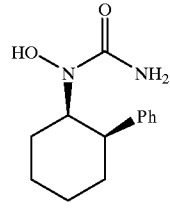

m.p. 125.5–125.9° C.

IR (KBr) v 3520, 3490, 3400, 2930, 2920, 2850, 1640, 1620, 1550, 1460 cm$^{-1}$.

$^1$H NMR (DMSO-d$_6$) δ 8.86 (s, 1H), 7.34-7.07 (m, 5H), 5.84 (s, 2H), 4.5614 4.48 (m, 1H), 2.95-2.82 (m, 1H), 2.39-2.19 (m, 1H), 2.06-1.65 (m, 3H), 1.64-1.32 (m, 2H).

Example 10

N-hydroxy-N-(trans-2-phenylcyclohexan-1-yl)urea

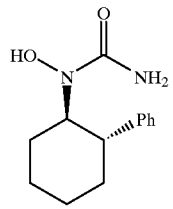

m.p. 1.63.1–164.1° C.

IR (KBr) v 3480, 3280, 3190, 2920, 1660, 1580, 1440 cm$^{-1}$.

$^1$H NMR (DMSO-d$_6$) δ 8.68 (s, 1H), 7.35-7.07 (m, 5H), 5.91 (s, 2H). 4.22 (td, J=11, 5 Hz, 1H), 2.26(td, J=13, 4 Hz, 1H), 1.86-1.57 (m, 5H), 1.55-1.12 (m, 3H)

Example 11

N-hydroxy-N-[(3-phenyl-2-cyclobuten)-1-yl)]urea

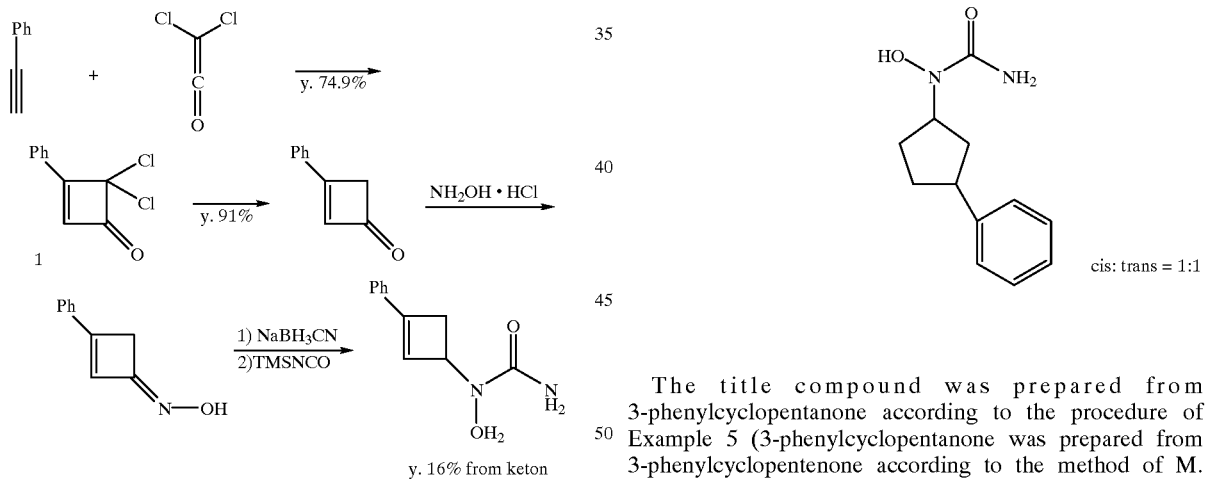

The title compound was prepared from 3-phenyl-2-cyclobuten-1-one (1) according to the procedure of Example 5 (3-Phenyl-2-cyclobuten-1-one was prepared according to the method of R. L. Danheiser et al., Tetrahedron Lett., 28, 3299 (1987)), m.p. 130–131°.

IR (Nujol) v 3200, 1620, 1570, 1240, 11160, 1070, 760 cm$^{-1}$.

$^1$H NMR (CDC$_3$) δ 9.02 (s, 1H), 7.35 (m, 5H), 6.29 (s, 1H), 5.78 (br, s, 2H), 5.23 (s, 1H), 3.00 (br s, 2H).

Example 12

N-hydroxy-N-(3-phenylcyclopentan-1-yl)urea

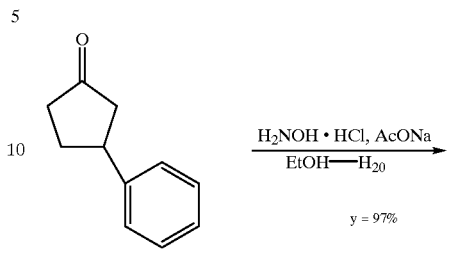

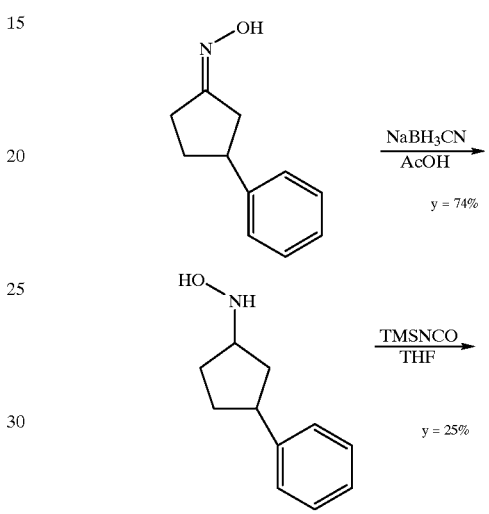

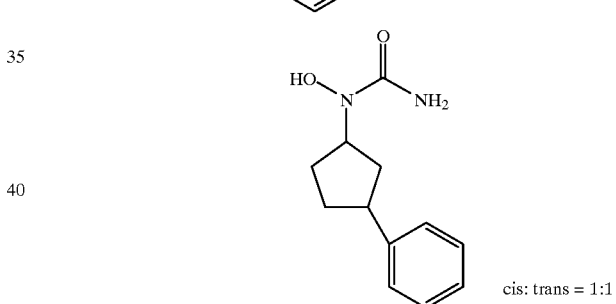

cis: trans = 1:1

The title compound was prepared from 3-phenylcyclopentanone according to the procedure of Example 5 (3-phenylcyclopentanone was prepared from 3-phenylcyclopentenone according to the method of M. Kolobielski et al., J. Am. Chem. Soc., 79, 5820 (1957)).

Example 13

N-hydroxy-N-[2-(4-phenyl-1-cyclohexan-1-yl)ethyl] urea

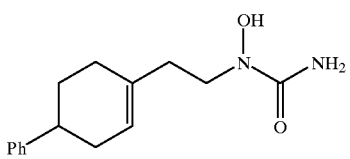

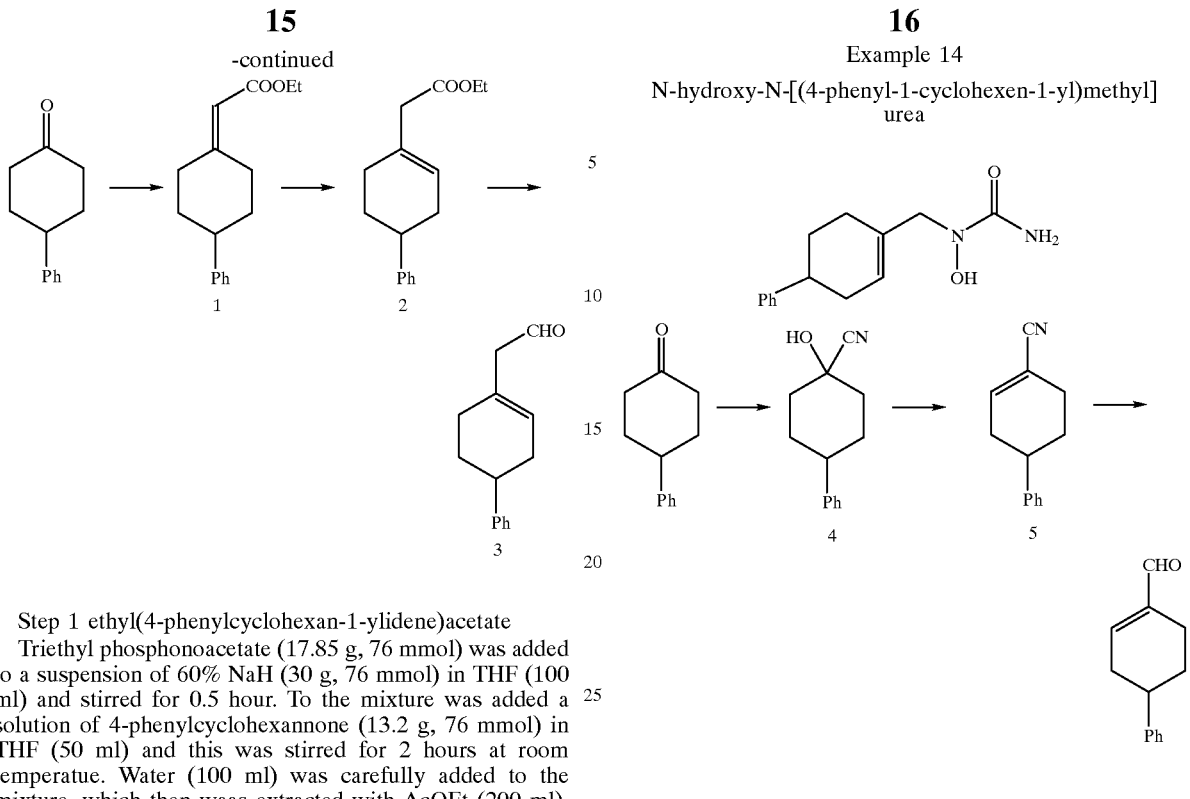

Step 1 ethyl(4-phenylcyclohexan-1-ylidene)acetate

Triethyl phosphonoacetate (17.85 g, 76 mmol) was added to a suspension of 60% NaH (30 g, 76 mmol) in THF (100 ml) and stirred for 0.5 hour. To the mixture was added a solution of 4-phenylcyclohexannone (13.2 g, 76 mmol) in THF (50 ml) and this was stirred for 2 hours at room temperatue. Water (100 ml) was carefully added to the mixture, which then waas extracted with AcOEt (200 ml). The combined organic layers were dried over $MgSO_4$ and concentrated in vacuo to give 19.7 g (quantitative yield) of product (1) as a colorless oil.

Step 2 ethyl(4-phenyl-1-cyclohexen-1-yl)acetate

The unsaturated ester prepared in Step 1, above (19.7 g, 76 mmol), was dissolved in EtOH (100 ml) and a catalytic amount of sodium ethoxide was added. The mixture was heated under reflux for 3 hours, then the volatiles were removed and the residue was diluted with AcOEt (100 ml). The organic layer was washed with water (50 ml), dried over $MgSO_4$ and concentrated in vacuo. Chromatographic seperation on silica gel provided 3.75 g (21% yield) of product (2) and 6.07 g (35% yield) of recovered exo-olefin (1) as colorless oils.

$^1$H NMR (CDCl$_3$) δ 7.16-7.34 (m, 5H), 5.64-5.68 (m, 1H), 4.16 (q, J=7 Hz, 2H), 3.00 (s, 2H), 27.0-2.85 (m, 1H), 2.05-2.43 (m, 4H), 1.91-2.03 (m, 1H), 1.72-1.88 (m, 1H), 1.27 (t, J=7Hz, 3H).

Step 3, (4-Phenyl-1-cyclohexen-1-yl)acetaldehyde

To a cooled (-78° C.) solution of the ester (2) prepared in Step 2, above (3.7 g, 16 mmol), in dry toluene (60 ml) was added dropwise a 1.02 M solution of DlBAL in dry toluene (15.7 ml, 16 mmol) at −78° under Ar atmosphere. The solution was stirred for 1 hour at that temperature. Water (2 ml) was carefully added and the reaction mixture was stirred for 0.5 hour. The resulting suspension was filtered through a celite pad and the organic layer was concentrated in vacuo to give 3.0 g (94% yield) of the desired aldehyde (3) as a colorless oil.

Step 4, N-hydroxy-N-[2-(4-phenyl-1-cyclohexan-1-yl)ethyl]urea

The title compound (m.p. 131.8–132.6° C. ) was prepared from the aldehyde prepared in Step 3, above, according to the procedure of Example 5.

IR (KBr) v 3450, 3200, 2900, 1640, 1580, 1475 cm$^{-1}$.

$^1$H NMR (DMSO-d$_6$) δ 9.21 (s, 1H), 7.33-7.10 (m, 5H), 6.23 (s, 2H), 5.50 (s, 1H), 3.57-3.35 (m, 1H), 277-2.60 (m, 1H), 2.29-1.92 (m, 6H), 1.89-15.6 (m, 2H).

Example 14

N-hydroxy-N-[(4-phenyl-1-cyclohexen-1-yl)methyl]urea

Step 1, 1-hydroxy-4-phenylcyclohexanecarbonitrile

To a solution of 4-phenylcyclohexanone (11.4 g, 65.5 mmol) and sodium cyanide (3.53 g, 72 mmol) in MeOH (25 ml) was added dropwise acetic acid (5.0 g, 8.3 mmol) at 0° C. The reaction mixture was stirred for 2 hours at room temperature and then volatiles were removed under reduced pressure. The residue was diluted with water (50 ml ) and extracted with Et$_2$O (100 ml). The organic layer was dried over $MgSO_4$ and concentrated in vacuo to give 13.5 g (quantitative yield) of product (1) as yello crystals.

Step 2, 4-phenyl-1-cyclohexenecarbonitrile

To a solution of the cyanohydrin prepared in Step 1, above (13.5 g, 65.5 mmol), in pyridine (40 ml) was added dropwise phosphorous oxychloride (7.2 g, 50 mmol) at 0° C. The mixture was heated at 80° C. for 2 hours. The r eaction mixture was poured over ice (100 g) and extracted with Et$_2$ (200 ml). The organic layer was washed with brine, dried over MgS0$_4$, and concentrated in vacuo to give 11.5 g (96% yield) of desired product (2) as yellow crystals.

Step 3, 4-phenyl-1-cyclohexencarboxaldehyde

The nitrile prepared in Step 2, above (7.3 g, 40 mmol), was treated with DlBAL (0.96 M in toluene, 51 ml, 48 mmol) in $CH_2Cl_2$ (100 ml) according to the procedure described in Example 13, Step 3. The aldehyde (3) was recovered in 85% yield as a pale yellow oil.

Step 4, N-hydroxy-N-[(4-phenyl-1-cyclohexen-1-yl)methyl]urea

The title compound (m.p. 142.3–143.1° C.) was prepared from the aldehyde prepared in Step 3, above, according to the procedure of Example 5.

IR (KBr) v 3480, 3430, 3400, 2910, 1610, 1650 cm$^{-1}$.

$^1$H NMR (DMSO-d$_6$) δ 9.15 (s, 1H), 7.33-7.14 (m, 5H), 6.24 (s, 2H), 5.66-5.57 (m, 1H), 3.90 (s, 2H), 2.78-2.64 (m, 1H), 2.32-1.95 (m, 4H), 1.92-1.79 (m, 1H), 1.79-1.60 (m, 1H).

Example 15

N-hydroxy-N-[exo-1,1a, 6,6a-tetrahydrocycloprop[a]inden-1-yl)methyl]urea

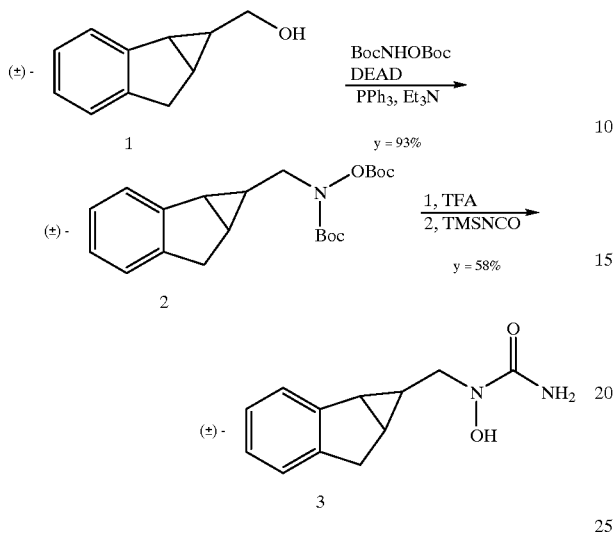

Step 1, N, O-di-tert-butoxycarbonyl-N-[exo-1,1a,6,6a-tetrahydrocycloprop[a]inden-1-yl))methyl]hydroxylamine To a stirred solution of exo-1-hydroxymethyl-1,1a,6,6a-tetrahydrocycloprop[a]indene (1) (1.53 g, 9.6 mmol, prepared according to the method of S. S. Hixon et al., J. Am. Chem. Soc., 110, 3601 (1988)), N,O-di-tert-butoxycarbonylhydroxylamine (3.86 g, 14.4 mmol) and triphenylphosphine (3.78 g, 14.4 mmol) in toluene (20 ml) was added dropwise a solution of diethylzaodicarboxylate (2.51 g, 14.4 mmol) in toluene (5 ml) over 10 minutes at −42° C. under a nitrogen atmosphere. The reaction mixture was stirred for 17.5 hours at −42° C. to room temperature. The precipitates were filtered off and the filtrate was concentrated under reduced pressure. The residue was purified by column chromatography on silica gel (300 g) using 5% ethyl acetate in n-hexane as an eluent to give 3.33 g (8.9 mmol, 93% yield of the title compound (2).

IR (KBr) v 1786, 1711 cm$^{-1}$.

$^1$H NMR (CDCl$_3$) δ 7.29-7.27 (m, 1H), 7.14-7.05 (m, 3H), 3.64 (dd, J=6.96, 15.02 Hz, 1H), 3.50 (dd, J=6.96, 15.02 Hz, 1H) 3.14 (dd, J=6.96, 16.85 Hz, 1H), 2.97 (d, J=16.85 Hz, 1H), 2.38-2.33 (m, 1H), 1.85-1.78 (m, 1H), 1.52 (s, 9H), 1.49 (s. 9H), 0.76 (tt, J=3.45, 6.96 Hz, 1H).

Step 2, N-hydroxy-N-[exo-(1,1a, 6,6a-tetrahydrocycloprop[a ]inden-1-yl)methyl]urea To a solution of the hudroxylamine (2) prepared in Step 1, above (3.29 g, 8.8 mmol), in dichloromethane (40 ml) was slowly added trifluoracetic acide (6.8 ml) at 0° C. under stirring. After stirring for 27 hours at 0° C. to room temperature, the soluent was evaporated off. The residue was combined with saturated sodium bicarbonate (50 ml) and extracted with ethyl acetate (2×100 ml). The combined extracts were washed with saturated sodium bicarbonate (50 ml) and brine (50 ml), and dried over magnesium sulfate. Evaporation of the solvent gave 1.51 g of crude N-[(exo-1,1a,6,6a-tetrahydrocycloprop[a]inden-1-yl)methyl]hydroxylamine.

To a stirred solution of the hydroxylamine prepared according to the preceding paragraph in tetrahydrofuran (50 ml) was added trimethylsilyliso-cyanate (95%, 1.17 g, 9.7 mmol), and the reaction mixture was stirred at room temperature for 3.5 hours. To the stirred reaction mixture was added methanol (10 ml) and 10 minutes later the solvent was evaporated off. Recrystallization from ethyl acetate afforded 1.11 g (5.1 mmol, 58% yield) of the title compound, m.p. 139–140° C.

IR (KBr) v 3475, 3347, 3280,1616, 1601, 1576 cm$^{-1}$.

$^1$H NMR (DMSO-d$_6$) δ 9.30 (s, 1H), 7.27-7.26 (m, 1H), 7.15-7.01 (m, 3H), 6.28 (s, 2H), 3.34 (dd, J=6.96, 15.02 Hz, 1H), 3.31 (dd, J=6.96, 15.02 Hz, 1H), 3.08 (dd, J=6.96, 16.85 Hz, 1H), 2.90 (d, J=16.85 Hz, 1H), 2.38-2.30 (m, 1H), 1.99-1.75 (, 1H), 0.62-0.56 (m, 1H).

Anal. Calc. for C$_{12}$H$_{14}$N$_2$O$_2$: C, 66.03; H, 6.46; N, 12.83. Found: C, 65.79; H, 6.51; N, 12.71.

Example 16

N-hydroxy-N-[endo-1,1a,6,6a-tetrahydrocycloprop[a]inden-1-yl)methyl]urea

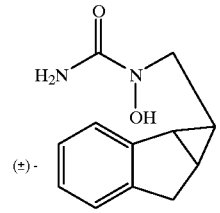

The title compound (m.p. 151–152° C.) was prepared according to the procedure of Example 15.

IR (KBr) v 3480, 3310, 3160, 1640, 1570 cm$^{-1}$.

$^1$H NMR (DMSO) δ 9.12 (s, 1H), 7.26–7.21 (m, 1H), 7.10–7.04 (m, 1H), 6.19 (s, 1H), 3.05 (dd, J=6.96, 17.58 Hz, 1H), 2.95 (d, J=17.58 Hz, 1H), 2.82 (dd, J=5.86, 14.29 Hz, 1H), 2.79 (dd, J=7.69, 14.29 Hz, 1H), 2.26 (ddd, J=1.62, 6.96, 7.96 Hz, 1H), 1.19 (dddd, J=1.62, 6.60, 6.96, 7.96 Hz, 1H), 1.41 (ddd, J=5.86, 6.60, 6.96, 7.69 Hz, 1H).

Example 17

N-[(2,2-dichloro-trans-3-phenylcyclopropyl)methyl]-N-hydroxyurea

Step 1, (2,2-dichloro-trans-3-phenyl-1-cyclopropyl)methyl acetate

A solution of sodium trichloroacetate (27.8 g, 150 mmol) in diglyme (20 ml) was added dropwise over 1 hour to a solution of trans-cinnamyl acetate (8.81 g, 50 mmol) in diglyme (80 ml) at 120° C. to 135° C. and the reaction mixture was heated at 120° C. to 125° C. for 1 hour. The reaction mixture was cooled to room temperature, poured into water (300 ml), extracted with n-hexane (300 ml+3×50 ml) and dried over MgSO$_4$. The solvent was removed and the residue was distilled under vacuum affording the title compound (11.0 g, 76% yield, b.p. 104–105° C. (0.15 mmHg)).

IR (film) v 1740 cm$^{-1}$.

$^1$H NMR (CDCl$_3$) δ 7.40–7.23 (m, 5H), 4.47 (dd, J=6.23, 12.29 Hz, 1H), 4.30 (dd, J=8.42, 12.09 Hz, 1H), 2.71 (d, J=8.42 Hz, 1H), 2.34 (dt, J=6.23, 8.06 Hz, 1H), 2.13 (s, 3H).

Step 2, N,O-di-tert-butoxycarbonyl-N-[(2,2-dichloro-trans-3-phenylcyclopropyl)methyl]hydroxylamine A solution of KOH (3.36 g, 60 mmol) and the product of Step 1, above, (10.36 g, 40 mmol) in a mixture of methanol (30 ml), tetrahydrofuran (30 ml) and water (90 ml) was stirred for 3 hours at room temperature. The reaction mixture was neutralized with 1N aqueous hydrochloric acid and extracted with diethyl ether (100 ml+2×50 ml). The combined organic phases were washed with saturated aqueous sodium bicarbonate (2×50 ml) and brine (50 ml), then dried over $MgSO_4$. Evaporation of the solvent afforded (2,2-dichloro-trans-3-phenylcyclopropyl)methanol in quantitative yield. To a stirred solution of the alcohol thus prepared (4.34 g, 20 mmol), N,O-di-tert-butoxycarbonylhydroxylamine (5.83 g, 25 mmol), and triphenylphosphine (6.56 g, 25 mmol) in toluene (40 ml), cooled to −42° C. was added dropwise a solution of diethyl azodicarboxylate (4.35 g, 25 mmol) in toluene (5 ml) over 15 minutes under a nitrogen atmosphere. The reaction mixture was allowed to warm to room temperature overnight, insolubles were removed by filtration and the filtrate concentrated under reduced pressure. The resultant residue was purified by column chromatography ($SiO_2$, 300 g; 8% ethyl acetate in n-hexane) affording the title compound (8.09 g, 94% yield).

IR (KBr) ν 1783, 1717 $cm^{-1}$.

$^1$H NMR ($CDCl_3$) δ 7.38–7.24 (m, 5H), 4.01 (dd, J=6.60, 15.39 Hz, 1H), 3.98 (dd, J=6.60, 15.39 Hz, 1H), 2.69 (d, J=8.43, 6.60 Hz, 1H), 1.48 (s, 18H).

Step 3, N-[(2,2-dichloro-trans-3-phenylcyclopropyl) methyl]-N-hydroxyurea

To a stirred solution of the product of Step 2, above (3.75 g, 8.7 mmol) in dichloromethane (40 ml) cooled to 0° C. was slowly added trifluoroacetic acid (6.7 ml). The reaction mixture was allowed to warm to room temperature overnight, and the solvent was evaporated off. The resultant residue was covered with saturated aqueous sodium bicarbonate (50 ml) and extracted with ethyl acetate (2×100 ml). The combined extracts were washed with saturated aqueous sodium bicarbonate (50 ml) and brine (50 ml), then dried over $MgSO_4$. Evaporation of the solvent afforded 3.02 g of crude N-[(2,2-dichloro-trans-3-phenylcyclopropyl)methyl] hydroxylamine. To a stirred solution of the hydroxylamine thus obtained, in tetrahydofuran (50 ml), was added trimethylsilylisocyanate (85%, 1.77 g, 13.1 mmol), and the reaction mixture was stirred at room temperature for 1.5 hours. Methanol (10 ml) was added and 10 minutes later the solvent was evaporated off. Purification by column chromatography ($SiO_2$, 300 g; 10% n-hexane in ethyl acetate) gave 1.90 g of white solids. Recrystallization from 50% ethyl acetate in n-hexane afforded 1.41 g (59% yield) of the title compound, m.p. 128–130° C.

IR (KBr) ν 3459, 3360, 3170, 2890, 1624, 1566 $cm^{-1}$.

$^1$H NMR (DMSO-$d_6$) δ 9.58 (s, 1H), 7.40–7.27 (m, 5H), 6.47 (s, 2H), 3.78 (dd, J=6.96, 14.29 Hz, 1H), 3.67 (dd, J=6.96, 14.29 Hz, 1H), 2.88 (d, J=8.43 Hz, 1H), 2.34 (dt, J=6.96, 8.43 Hz, 1H).

Anal. Calc. for $C_{11}H_{12}Cl_2N_2O_2$: C, 48.02; H, 4.39; N, 10.18. Found: C, 47.84; H, 4.35; N, 10.09.

Example 18

N-Hydroxy-N-([trans-2-(3-methylthiophenyl) cyclopropyl]methyl)urea

Step 1, [2-trans-(3-Methylthiophenyl)cyclopropyl] methanol

To a stirred mixture of 1.7 M pentane solution of tert-butyllithium (2.1 ml, 3.5 mmol) and diethyl ether (10 ml) was added a solution of [2-trans-(3-bromophenyl) cyclopropyl]methanol (277 mg, 1 mmol) in diethyl ether (5 ml) below −70° C. over 5 minutes. After stirring at −78° C. for 1 hour, dimethyl disulfide (207 mg, 2.2 mmol) was slowly added, and the reaction mixture allowed to warm to room temperature overnight. The resultant mixture was quenched with water (20 ml) and extracted with diethyl ether (20 ml+10 ml). The combined organic layers were washed with brine, dried over $MgSO_4$ and evaporated. The residue was purified by column chromatography ($SiO_2$, 50 g; 20% ethyl acetate in n-hexane). Evaporation of the eluent gave the title compound (148 mg, 76% yield).

IR (film) ν 3375, 1594, 1022 $cm^{-1}$.

$^1$H NMR ($CDCl_3$) δ 7.18 (t, J=7.70 Hz, 1H), 7.08–7.03 (m, 1H), 7.00–6.98 (m, 1H), 6.58–6.81 (m, 1H), 3.62 (dd, J=5.86, 6.23 Hz, 2H), 2.47 (s, 3H), 1.85–1.77 (m, 1H), 1.50–1.44 (m, 1H), 1.42 (t, J=5.86 Hz, 1H), 1.01–0.89 (m, 2H).

Step 2, N-O-di-tert-butoxycarbonyl-N-([2-trans-(3-methylthiophenyl)cyclopropyl]methyl)hydroxylamine This compound was prepared (75% yield) from the product of Step 1, above, using the method described in Example 15, Step 1.

IR (KBr) ν 1784, 1714 $cm^{-1}$.

$^1$H NMR ($CDCl_3$) δ 7.15 (t, J=7.70 Hz, 1H), 7.06–7.02 (m, 1H), 6.99–6.97 (m, 1H), 6.84–6.80 (m, 1H), 3.71 (dd, J=6.60, 14.66 Hz, 1H), 3.57 (dd, J=6.60, 14.66 Hz, 1H), 2.33 (s, 3H), 1.86–1.83 (m, 1H), 1.50–1.37 (m, 1H), 1.48 (s, 9H), 1.47 (s, 9H), 0.98–0.85 (m, 2H).

Step 3, N-hydroxy-N-([2-trans-(3-methylthiophenyl) cyclopropyl]methyl)urea

The hydroxylamine prepared in Step 2 was converted to the title compound according to the procedure described in Example 15, Step 2. The crude product was recrystallized from ethyl acetate to afford the title compound in 58% yield, m.p. 126–127° C.

IR (KBr) ν 3465, 3350, 3180, 3000, 2994, 1602, 1583, 1505, 1480, 1443, 1425 $cm^{-1}$.

$^1$H NMR (DMSO-$d_6$) δ 9.29 (s, 1H), 7.17 (t, J=7.70 Hz, 1H), 7.03–6.89 (m, 1H), 6.95–6.92 (m, 1H), 6.83–6.78 (m, 1H), 6.27 (s, 2H), 3.38 (dd, J=6.60, 14.66 Hz, 1H), 3.34 (dd, J=6.60, 14.66 Hz, 1H), 2.45 (s, 3H), 1.99–1.80 (m, 1H), 1.39–1.28 (m, 1H), 0.92–0.86 (m, 2H).

Anal. Calc. for $C_{12}H_{16}N_2O_2S$: C, 57.12; H, 6.39; N, 11.10; Found: C, 56.97; H, 6.48; N, 10.74.

The following compounds were prepared by methods analogous to the foregoing examples.

Example 19

N-hydroxy-N-[(2-methyl-trans-2-phenylcyclopropyl) methyl]urea m.p. 86–87° C.

IR (KBr) ν 3475, 3340, 3185, 1621, 1566, 1474, 1443, 1428 $cm^{-1}$.

$^1$H NMR (DMSO-$d_6$) δ 9.28 (s, 1H), 7.30–7.10 (m, 5H), 6.28 (2, 2H), 3.61 (dd, J=7.69, 14.29 Hz, 1H), 3.44 (dd, J=7.69, 14.29 Hz, 1H), 1.36 (s, 3H), 1.25 (ddt, J=7.69, 9.16, 5.85 Hz, 1H), 1.04 (dd, J=4.77, 9.16 Hz, 1H), 0.54 (dd, J=4.77, 5.86 Hz, 1H).

Example 20

N-hydroxy-N-[(2-methyl-cis-2-phenylcyclopropyl)methyl]urea m.p. 151–152° C.

IR (KBr) v 3475, 3310, 3245, 3160, 1637, 1640, 1571, 1495, 1444, 1420 cm$^{-1}$.

$^1$H NMR (DMSO-d$_6$) δ 9.19 (s, 1H), 7.33–7.15 (m, 5H), 6.23 (s,2H), 3.25 (dd, J=4.03, 13.92 Hz, 1H), 2.45 (d, J=4.03, 13.92 Hz, 1H), 1.32 (s, 3H), 1.29–1.18 (m, 1H), 0.93 (dd, J=4.76, 5.13 Hz, 1H), 0.75 (dd, J=4.76, 8.06 Hz, 1H).

Example 21

N-[(3,3-dimethyl-trans-2-phenylcyclopropyl)methyl]-N-hydroxyurea m.p. 132.5–133° C.

IR (KBr) v 3505, 3470, 3385, 3345, 1637, 1458 cm$^{-1}$.

$^1$H NMR (DMSO-d$_6$) δ 9.27 (s, 1H), 7.28–7.14 (m, 5H), 6.27 (s, 2H), 3.58 (dd, J=6.96, 14.29 Hz, 1H), 3.46 (dd, J=6.96, 14.29 Hz, 1H), 1.72 (d, J=5.86 Hz, 1H), 1.35 (dt, J=5.86, 6.96 Hz, 1H), 1.20 (s, 3H), 0.75 (s, 3H).

Example 22

N-hydroxy-N-[(1-methyl-trans-2-phenylcyclopropyl)methyl]urea m.p. 119–120° C.

IR (KBr) v 3475, 3360, 3305, 1668, 1640, 1578 cm$^{-1}$.

$^1$H NMR (DMSO-d$_6$) δ 9.23 (s, 1H), 7.30–7.12 (m, 5H), 6.23 (s, 2H), 3.49 (d, J=14.29 Hz, 1H), 3.29 (d, J=14.29 Hz, 1H), 2.04 (dd, J=6.60, 8.06 Hz, 1H), 0.91–0.77 (m, 2H), 0.72 (s, 3H).

Example 23

N-Hydroxy-N-([trans-2-(2-methylphenyl)cyclopropyl]methyl)urea m.p. 106–106.5° C.

IR (KBr) v 3480, 3365, 3165, 2885, 1661, 1627, 1575, 1493, 1457, 1434 cm$^{-1}$.

$^1$H NMR (DMSO-d$_6$) δ 9.31 (s, 1H), 7.13–7.00 (m, 3H), 6.92–6.88 (m, 1H), 6.26 (s, 2H), 3.35 (dd, J=6.96, 15.02 Hz, 1H), 3.41 (dd, J=6.96, 15.02 Hz, 1H), 2.35 (s, 3H), 1.89–1.81 (m, 1H), 1.30–1.19 ( m, 1H), 0.91–0.80 (m, 2H).

Example 24

N-[(2,2-diphenylcyclopropyl)methyl]-N-hydroxyurea m.p. 164–165° C. (dec.).

IR(IBr) v 3465, 3310, 3110, 3080, 3030, 2900, 2830, 1631, 1577, 1489, 1441 cm$^{-1}$.

$^1$H NMR (DMSO-d$_6$) δ 9.33 (s, 1H), 7.39–7.09 (m, 10H), 6.27 (s, 2H), 3.49 (dd, J=4.40, 13.92 Hz, 1H), 2.71 (dd, J=4.77, 13.92 Hz, 1H), 1.89–1.82 (m, 1H), 1.37 (dd, J=4.76, 5.86 Hz, 1H), 1.24 (dd, J=4.76, 8.79 Hz, 1H).

Example 25

N-hydroxy-N-([trans-2-(3-methylphenyl)cyclopropyl]methyl)urea m.p. 113–114° C.

IR (KBr) v 3460, 3350, 3180, 1605, 1580, 1505, 1491, 1444, 1427 cm$^{-1}$.

$^1$H NMR (DMSO-d$_6$) δ 9.27 (s, 1H), 7.10 (dd, J=7.33, 7.69 Hz, 1H), 6.94–6.90 (m, 1H), 6.87–6.81 (m, 2H), 6.26 (s, 2H), 3.34 (d, J=6.96 Hz, 2H), 2.24 (s, 3H), 1.84–1.76 (m, 1H), 1.33–1.27 (m, 1H), 0.90–0.82 (m 2H).

Example 26

N-hydroxy-N-([trans-2-(4-methylphenyl)cyclopropyl]methyl)]urea m.p. 149–150° C.

IR (KBr) v 3450, 3335, 3165, 2920, 2880, 1613, 1572, 1498, 1435 cm$^{-1}$.

$^1$H NMR (DMSO-d$_6$) δ 9.26 (s, 1H), 7.10 (d, J=8.43 Hz, 2H), 6.93 (d, J=8.43 Hz, 2H), 6.26 (s, 2H), 3.34 (d, J=6.96 Hz, 2H), 2.23 (s, 3H), 1.83–1.76 (m, 1H), 1.32–1.21 (m, 1H), 0.89–0.78 (m, 2H).

Example 27

N-([trans-2-(3-bromophenyl)cyclopropyl]methyl)-N-hydroxyurea m.p. 96–96.5° C.

IR (KBr) v 3465, 3350, 3185, 1643, 1603, 1583, 1505, 1481, 1446, 1426 cm$^{-1}$.

$^1$H NMR (DMSO-d$_6$) δ 9.30 (s, 1H), 7.30–7.16 (m, 3H), 7.07–7.03 (m, 1H), 6.28 (s, 2H), 3.40 (dd, J=6.96, 14.92 Hz, 1H), 3.32 (dd, J=6.96, 14.92 Hz, 1H), 1.90–1.83 (m, 1H), 1.37–1.28 (m, 1H), 0.95–0.90 (m, 2H).

Example 28

N-([trans-2-(4-bromophenyl)cyclopropyl]methyl)-N-hydroxyurea m.p. 130–131° C.

IR (KBr) v 3445, 3335, 3255, 3160, 2935, 2880, 1615, 1572, 1491, 1437 cm$^{-1}$.

$^1$H NMR (DMSO-d$_6$) δ 9.29 (s, 1H), 7.41 (d, J=8.43 Hz, 2H), 6.27 (s, 2H), 3.38 (dd, J=7.33, 15.02 Hz, 1H), 3.30 (dd, J=7.33, 15.02 Hz, 1H), 1.89–1.81 (m, 1H), 1.38–1.26 (m, 1H), 0.96–0.84 (m, 2H).

Example 29

N-hydroxy-N-([trans-2-(2-naphthyl)cyclopropyl]methyl)urea m.p. 162–162.5° C.

IR (KBr) v 3460, 3340, 1627, 1599, 1577, 1434 cm$^{-1}$.

$^1$H NMR (DMSO-d$_6$) δ 9.32 (s, 1H), 7.85–7.7 (m, 3H), 7.59–7.55 (m, 1H), 7.49–7.37 (m, 2H), 7.23 (dd, J=1.93, 8.43 Hz, 1H), 6.29 (s, 2H), 3.45 (dd, J=6.60, 14.65 Hz, 1H), 3.41 (dd, J=6.60, 14.65 Hz, 1H), 2.06–1.99 (m, 1H), 1.50–1.43 (m, 1H), 1.06–0.95 (m, 2H).

Example 30

N-hydroxy-N-[(cis-2-phenylcyclopropyl)methyl]urea m.p. 100.6–101.4° C.

IR (KBr) ν 3500, 3200, 2900, 1670, 1640, 1580, 1500, 1280, 1160 cm$^{-1}$.

$^1$H NMR (DMSO-d$_6$) δ 8.17 (s, 1H), 7.28–7.13 (m, 5H), 5.28 (s, 2H), 3.33 (dd, J=5.1, 14.7 Hz, 1H), 2.96 (dd, J=8.8, 14.7 Hz, 1H), 2.23–2.15 (m, 1H), 1.48–1.37 (m, 1H), 1.04–0.94 (m, 2H).

Example 31

N-hydroxy-N-[(trans-2-phenylcyclopropyl)methyl]acetamide m.p.—(oil)

IR (KBr) ν 3200, 2900, 1620, 1460, 1360, 1260, 1180 cm$^{-1}$.

$^1$H NMR (DMSO-d$_6$) δ 7.30–7.05 (m, 5H), 3.71–3.60 (m, 2H), 2.14 (s, 3H), 1.95–1.88 (m, 1H), 1.62 (s, 1H), 1.49–1.37 (m, 1H), 1.03–0.92 (m, 2H).

Example 32

(1R*,1S*,2'S*)-N-hydroxy-N-[1-(2'-phenylcyclopropyl)ethyl]urea m.p. 144.0–144.6° C.

IR (KBr) ν 3450, 3350, 3200, 1660, 1440 cm$^{-1}$.

$^1$H NMR (DMSO-d$_6$) δ 8.97 (s, 1H), 7.24–6.99 (m, 5H), 6.26 (s, 2H), 3.70–3.59 (m, 1H), 1.98–1.88 (m, 1H), 1.38–1.25 (m, 1H), 1.15 (d, J=7.0 Hz, 3H), 0.91–0.80 (m, 2H).

Example 33

(1S*,1'S*,2'S*)-N-hydroxy-N-[1-(2'-phenylcyclopropyl)ethyl]urea m.p. 135.3–135.8° C.

IR (KBr) ν 3480, 3200, 1640, 1570, 1450, 1150 cm$^{-1}$.

$^1$H NMR (DMSO-d$_6$) δ 9.02 (s, 1H), 7.27–7.02 (m, 5H), 6.27 (m, 2H), 3.63–3.57 (m, 1H), 1.84–1.77 (m, 1H), 1.27–1.20 (m, 1H), 1.14 (d, J=6.6 Hz, 3H), 1.01–0.92 (m, 1H), 0.86–0.75 (m, 1H).

Example 34

N-([trans-2-(2-chlorophenyl)cyclopropyl]methyl)-N-hydroxyurea m.p. 105.6–105.9° C.

IR (KBr) ν 3490, 3200, 2900, 1665, 1630, 1580, 1480 cm$^{-1}$.

$^1$H NMR (DMSO-d$_6$) δ 9.31 (s, 1H), 7.39 (dd, J=1.5, 7.7 Hz, 1H), 7.26–7.17 (m, 2H), 7.03 (dd, J=2.0, 7.7 Hz, 1H), 6.27 (s, 2H), 3.50 (dd, J=6.6, 14.3 Hz, 1H), 3.41 (dd, J=5.1, 12.1 Hz, 1H), 2.10–2.04 (m, 1H), 1.43–1.33 (m, 1H), 1.02–0.85 (m, 2H).

Example 35

N-([trans-2-(3-chlorophenyl)cyclopropyl]methyl)-N-hydroxyurea m.p. 109.9–110.7° C.

IR (KBr) ν 3460, 3350, 3180, 1600, 1580, 1520, 1450, 1430 cm$^{-1}$.

$^1$H NMR (DMSO-d$_6$) δ 7.20–6.92 (m, 4H), 5.29 (br s, 2H), 3.67 (dd, J=6.2, 14.7 Hz), 3.45 (dd, J=7.7, 14.7 Hz, 1H), 1.85–1.91 (m, 1H), 1.61 (br s, 1H), 1.51–1.40 (m, 1H), 1.05–0.93 (m, 2H).

Example 36

N-([trans-2-(4-chlorophenyl)cyclopropyl]methyl)-N-hydroxyurea m.p. 115.0–115.7° C.

IR (KBr) ν 3450, 3330, 3170, 2900, 1620, 1575, 1500 cm$^{-1}$.

$^1$H NMR (DMSO-d$_6$) δ 9.30 (s, 1H), 7.27 (d, J=8.4 Hz, 2H), 7.07 (d, J=8.8 Hz, 2H), 6.28 (s, 2H), 3.44–3.28 (m, 2H), 1.90–1.83 (m, 1H), 1.41–1.30 (m, 1H), 0.96–0.86 (m, 2H).

Example 37

N-hydroxy-N-([trans-2-(2-trifluoromethylphenyl)cyclopropyl]methyl)urea m.p. 103.5–104.4° C.

IR (KBr) ν 3450, 3370, 2820, 1660, 1630, 1590, 1540, 1460, 1370, 1265, 1210 cm$^{-1}$.

$^1$H NMR (DMSO-d$_6$) δ 9.30 (s, 1H), 7.64 (d, J=7.7 Hz, 1H), 7.55 (t, J=7.7 Hz, 1H), 7.35 (t, J=7.7 Hz, 1H), 7.18 (d, J=7.7 Hz, 1H), 6.27 (s, 2H), 3.53–3.29 (m, 2H), 2.07–1.96 (m, 1H), 1.52–1.38 (m, 1H), 1.06–0.94 (m, 2H).

Example 38

N-hydroxy-N-([trans-2-(3-trifluoromethylphenyl)cyclopropyl]methyl)urea m.p. 101.5–102.3° C.

IR (KBr) ν 3500, 3300, 2900, 1630, 1460, 1360, 1330, 1130 cm$^{-1}$.

$^1$H NMR (DMSO-d$_6$) δ 7.68 (br s, 1H), 7.40–7.20 (m, 4H), 5.38 (br s, 2H), 3.61 (dd, J=6.4, 14.7 Hz, 1H), 3.46 (dd, J=7.3, 14.7 Hz, 1H), 1.97–1.90 (m, 1H), 1.49–1.43 (m, 1H), 1.05–0.95 (m, 2H).

Example 39

N-hydroxy-N-([trans-2-(4-trifluoromethylphenyl)cyclopropyl]methyl)urea m.p. 136.3–136.8° C.

IR (KBr) ν 3500, 3330, 2900, 1670, 1635, 1560, 1480, 1330, 1160, 1120 cm$^{-1}$.

$^1$H NMR (DMSO-d$_6$) δ 9.31 (s, 1H), 7.57 (d, J=8.1 Hz, 2H), 7.27 (d, J=8.1 Hz, 2H), 6.28 (s, 2H), 3.47–3.34 (m, 2H), 2.00–1.94 (m, 1H), 1.48–1.35 (m, 1H), 1.04–0.94 (m, 2H).

Example 40

N-[(trans-2-(3-fluorophenyl)cyclopropyl]methyl)-N-hydroxyurea m.p. 123.5–124.0° C.

IR (KBr) v 3480, 3300, 2900, 1630, 1580, 1460, 1135 cm$^{-1}$.

$^1$H NMR (DMSO-d$_6$) δ 9.30 (s, 1H), 7.30–7.21 (m, 1H), 6.95–6.83 (m, 3H), 6.28 (s, 2H), 3.44–3.28 (m, 2H), 1.89–1.85 (m, 1H), 1.36–1.31 (m, 1H), 0.95–0.90 (m, 2H).

Example 41

N-([trans-2-(4-flurophenyl)cyclopropyl]methyl)-N-hydroxyurea m.p. 139.8–140.5° C.

IR (KBr) v 3450, 3320, 3180, 2900, 1630, 1580, 1455 cm$^{-1}$.

$^1$H NMR (DMSO-d$_6$) δ 7.05–6.90 (m, 4H), 6.28 (br s, 1H), 5.27 (br s, 2H), 3.66 (dd, J=6.2, 14.7 Hz, 1H), 3.48 (dd, J=7.7, 14.7 Hz, 1H), 1.93–1.85 (m, 1H), 1.46–1.35 (m, 1H), 1.00–0.88 (m, 2H).

Example 42

N-hydroxy-N-([trans-2-(3-methoxyphenyl)cyclopropyl]methyl)urea m.p. 109.5–110.0° C.

IR (KBr) v 3450, 3300, 2900, 1640, 1605, 1580, 1495, 1450, 1405, 1355, 1260, 1090 cm$^{-1}$.

$^1$H NMR (DMSO-d$_6$) δ 9.29 (s, 1H), 7.16–7.10 (m, 1H), 6.70–6.61 (m, 3H), 6.26 (s, 2H), 3.72 (s, 3H), 3.45–3.31 (m, 2H), 1.83–1.78 (m, 1H), 1.33–1.28 (m, 1H), 0.91–0.85 (m, 2H).

Example 43

N-hydroxy-N-([trans-2-(3-nitrophenyl)cyclopropyl]methyl)urea m.p. 123.5–124.5° C.

IR (KBr) v 3475, 3380, 3180, 1640, 1530, 1460 cm$^{-1}$.

$^1$H NMR (DMSO-d$_6$) δ 9.33 (s, 1H), 8.01–7.93 (m, 1H), 7.88 (s, 1H), 7.60–7.46 (m, 2H), 6.29 (s, 2H), 3.50–3.29 (m, 2H), 2.08–2.00 (m, 1H), 1.48–1.39 (m, 1H), 1.07–0.96 (m, 2H).

Example 44

N-([trans-2-(3,4-dichlorophenyl)cyclopropyl]methyl)-N-hydroxyurea m.p.—(oil).

IR (KBr) v 3475, 3350, 3200, 2900, 1630, 1575, 1480, 1235 cm$^{-1}$.

$^1$H NMR (DMSO-d$_6$) δ 7.34 (br s, 1H), 7.28 (d, J=8.0 Hz, 1H), 7.12 (d, J=2.2 Hz, 1H), 6.88 (dd, J=2.0, 8.2 Hz, 1H), 5.35 (s, 2H), 3.61 (dd, J=6.2, 14.7 Hz, 1H), 3.42 (dd, J=7.5, 14.5 Hz, 1H), 1.88–1.83 (m, 1H), 1.46–1.34 (m, 1H), 1.03–0.89 (m, 2H).

Example 45

N-([trans-2-(3-chloro-4-fluorophenyl)cyclopropyl]methyl)-N-hydroxyurea m.p. 82.3–82.9° C.

IR (KBr) v 3480, 3350, 1605, 1580, 1505, 1430 cm$^{-1}$.

$^1$H NMR (DMSO-d$_6$) δ 9.30 (s, 1H), 7.30–7.21 (m, 2H), 7.10–7.03 (m, 1), 6.28 (s, 2H), 3.45–3.24 (m, 2H), 1.90–1.84 (m, 1H), 1.32–1.28 (m, 1H), 0.94–0.87 (m, 2H).

The following shows a general reaction scheme for the stereoselective synthesis of various phenylcyclobutyl derivatives.

| Example | R | Yield (%) | | |
|---|---|---|---|---|
| | | Step 1 | Step 2 | Step 3 |
| 46 | H | 68.2 | quant. | 16.0 |
| 47 | CH$_3$ | 74.9 | quant. | 8.7 |
| 48 | n-propyl | 45.0 | quant. | 49.1 |

Example 46

N-hydroxy-N-(3-phenyl-2-cyclobutenyl)urea m.p. 130–131° C. (dec.).

IR (nujol) v 3200, 1620, 1570, 1240, 1160, 1070, 760 cm$^{-1}$.

$^1$H NMR (CDCl$_3$-DMSO-d$_6$) δ 9.02 (br s, 1H), 7.35 (m, 5H), 6.29 (s, 1H), 5.78 (br s, 2H), 5.23 (s, 1H), 3.00 (br s, 2H).

Example 47

N-hydroxy-N-(2-methyl-3-phenyl-2-cyclobutenyl)urea m.p. 138–139° C. (dec.)

IR (nujol) v 3190, 1640, 1635, 1565, 1180, 1080, 695 cm$^{-1}$, $^1$H NMR (CDCl$_2$) δ8.97 (s, 1H), 7.28 (s, 5H), 5.95 (s, 2H), 5.11 (br s, 1H), 2.82 (br s, 2H), 2.00 (s, 3H).

Example 48

N-hydroxy-N-(3-phenyl-2-propyl-2-propyl-2-cyclobutenyl)urea m.p. 132–133.5° C. (dec.).

IR (nujol) v 3470, 3170, 1630, 1565, 1190, 1080, 765 cm$^{-1}$, $^1$H NMR (CDCl$_3$-DMSO-d$_6$) δ8.67 (s, 1H), 7.35 (m, 5H), 5.44 (br s, 2H), 5.27 (d, J=2.5 Hz, 1H), 2.85 (m, 2H), 2.44 (m, 2H), 1.60 (m, 2H), 0.90 (t, J=7.4 Hz, 3H).

The following shows another general reaction scheme for the stereoselective synthesis of various phenylcyclobutyl derivatives.

| Example | | X | Yield (%) | | | | |
|---|---|---|---|---|---|---|---|
| cis | trans | | Step 1 | Step 2 | Step 3 | Step 4 | Step 5 |
| 49 | 50 | H | 54 | 60 | 32 | 74 | 25 |
| 51 | 52 | p-F | 64 | 77 | 11 | 69 | 27 |
| 53 | 54 | m-Cl | 92 | quant. | 28 | 76 | 26 |
| 55 | 56 | p-Cl | 75 | 76 | 25 | 87 | 23 |
| 58 | 57 | p-Br | 70 | 82 | 22 | 90 | 30 |
| 60 | 59 | p-CF$_3$ | 79 | 92 | 20 | 71 | 20 |
| | 61 | p-OCH$_3$ | 27 | 67 | 26 | | |
| 62 | | styryl | 94 | 59 | | quant. | 24 |

-continued

| Example | | | Yield (%) | | | | |
|---|---|---|---|---|---|---|---|
| cis | trans | X | Step 1 | Step 2 | Step 3 | Step 4 | Step 5 |
| 63 | | m-PhO—Ph | quant. | 90 | | quant. | 37 |

Example 49

N-hydroxy-N-(cis-3-phenylcyclobutyl)urea m.p. 169–171° C.

IR (nujol) v 3450, 3200, 1620, 1575, 1165, 750 cm$^{-1}$, $^1$H NMR (CDCl$_3$-DMSO-d$_6$) δ9.13 (s, 1H), 7.28–7.16 (m, 5H), 5.76 (br s, 2H), 4.77 (m, 1H), 3.06 (m, 1H), 2.48 (m, 4H).

Example 50

N-hydroxy-N-(trans-3-phenylcyclobutyl)urea m.p. 136–138° C.

IR (nujol) v 3450, 3200, 1615, 1570, 1150, 1060, 745, 695 cm$^{-1}$, $^1$H NMR (DMSO-d$_6$) δ9.19 (s, 1H), 7.28 (s, 5H), 5.60 (s, 2H), 5.20 (m, 1H), 3.47 (m, 1H), 2.87 (m, 2H), 2.33 (m, 2H).

Example 51

N-[cis-3-(4-fluorophenyl)cyclobutyl]-N-hydroxyurea

Step 1, N-[cis-3-(4-fluorophenyl)cyclobutyl]-N-hydroxyurea-3-(4-fluorophenyl)cyclobutanone In a 500 ml Erlenmeyer flask fitted with a magnetic stirrer was placed zinc powder (49.2 g, 0.75 g-atom) and 40 ml of 3% hydrochloric acid. The mixture was stirred rapidly for 1 minute, then the supernatant liquid was decanted. In a similar manner, the zinc powder was washed successively with three additional 40 ml portions of 3% hydrochloric acid, five 100 ml portions of distilled water, two 75 ml portions of 2% aqueous copper sulfate solution, five 100 ml portions of distilled water, four 100 ml of absolute ethanol, and five 100 ml portions of absolute ether. The couple was finally transferred to a Buchner funnel, washed with additional anhydrous ether, covered tightly with a rubber dam, and suction-dried until it reaches room temperature. The zinc-copper couple was stored overnight in a vacuum desiccator over phosphorus pentoxide and was then ready for use.

A 2000 ml three-necked flask equipped with a condenser, addition funnel, magnetic stirrer and N$_2$ inlet was flame dried while purging with N$_2$. When cool, the flask was charged with 35 g (0.287 mol) of 4-fluorostyrene, 20.6 g (0.315 mol) of zinc-copper couple, and 500 ml of anhydrous ether. The suspension was stirred under N$_2$ and a solution of 33.6 ml (54.8 g, 0.301 mol) of Cl$_2$COOCl and 27.8 ml (45.7 g, 0.298 mol) of POCl$_3$ in 240 ml of anhydrous ether was added dropwise over 1.5 hours. When addition was complete, the mixture was refluxed with stirring for 2 hours. The reaction mixture was then filtered through a pad of Celite and the unreacted zinc washed with 350 ml of ether. The ethereal solution was concentrated in vacuo to about 25% of its original volume, an equal volume (500 ml) of pentane was added and the solution was stirred for a few minutes to precipitate the zinc salts. The solution was decanted from the residue, washed successively with ice water (700 ml), a cold saturated aqueous NaHCO$_3$ solution (300 ml), water (300 ml) and brine (500 ml), was dried over MgSO$_4$ and the solvent removed in vacuo to leave 61 g of crude product as a pale yellow oil which was used without further purification.

To a stirred solution of the crude product prepared above, (61 g) in 250 ml of acetic acid was added 51.3 g of zinc powder at 10° C. (exothermic). After stirring for 30 minutes at 50–70° C., the mixture was filtered through a pade of Celite and the unreacted zinc was washed with acetic acid (50 ml) and ether (50 ml). Water (800 ml) was added to the mixture and the whole was extracted with ether (2×500 ml, 1×100 ml). The organic layer was washed with saturated aqueous NaHCO$_3$ solution (300 ml), water (300 ml) and brine (300 ml),then was dried over MgSO$_4$ and evaporated in vacuo to afford 39.5 g of the title compound (94.7% yield from 4-fluorostyrene).

$^1$H NMR (CDCl$_3$) δ7.26 (m, 2H), 7.04 (m, 2H), 3.65 (m, 1H), 3.55 (m, 2H), 3.23 (m, 2H).

Step 2 cis-3-(4-fluorophenyl)cyclobutanol

To a stirred solution of LiAl[O(CH$_3$)$_3$H (73.4 g, 0.289 mol) in 500 ml of THF cooled to −73° C. was added 39.5 g of the cyclobutanone prepared in Step 1, above (0.241 mol), in 150 ml of THF under an atmosphere of N$_2$. The reaction maxture was stirred over night at −70° C. and a cold saturated aqueous NH$_4$Cl solution (100 ml) was added. MgSO$_4$ (30 g) was added and the mixture was filtered through Celite, washed with ethyl acetate (4×50 ml) and the filtrate was evaporated in vacuo to afford crude product. Ethyl acetate (300 ml) was added, the solution dried over MgSO$_4$ and concentrated in vacuo to provide 38.5 g (96.3% yield) of the title cis-cyclobutanol as a pale yellow oil.

$^1$H NMR (CDCl$_3$) δ7.17 (m, 2H), 6.98 (m, 2H), 4.28 (m, 1H), 2.92 (m, 1H), 27.5 (m, 2H), 2.00 (m, 2H), 1.80 (br s, 1H).

Step 3, trans-3-(4-fluorophenyl)cyclobutyl benzoate

To a stirred solution of the cis-cyclobutanol prepared in Step 2, above (38.25 g, 0.23 mol), and Ph$_3$P (69.43 g, 0.265 mol) in THF (230 ml) was added benzoic acid (32.32 g. 0.265 mol) in one portion, and then DEAD (46.1 g, 0.265 mol) in THF 80 ml) was added dropwise at 10° C. (exothermic) under an atmosphere of N$_2$, After stirring for 1.5-hours at room temperature, the volatiles were evaporated in vacuo. Et$_2$O (200 ml) and n-hexane (50 ml) were added to the residue, insolubles were removed by filtration and the filtrate was concentrated in vacuo. This treatment was repeated two times to provide 87.3 g of crude title benzoate as a yellow oil, which was used without further purification.

$^1$H NMR (CDCl$_3$) δ8.1–7.1 (m, 9H), 5.41 (m, 1H), 3.74 (m, 1H), 2.68 (m, 4H).

Step 4, trans-3-(4-fluorophenyl)cyclobutanol

To a stirred solution of the crude benzoate prepared in Step 3, above (87 g), in THF (200 ml) and MeOH (200 ml) was added KOH (42 g) in water (300 ml) dropwise at room temperature. After stirring for 1.5 hours at room temperature solvent was evaporated off and the whole was extracted with ethyl acetate (2×400 ml, 1×150 ml). The organic layer was washed with water (300 ml) and brine (500 ml), then dried over MgSO$_4$ and evaporated in vacuo to afford approximately 61 g of crude product. Distillation (b.p. 87–88° C. (1.2 mmHg)) provided 33.88 g (88.6% yield from the cis-alcohol) of the title trans-alcohol as a colorless oil.

$^1$H NMR (CDCl$_3$) δ7.18 (m, 2H), 6.99 (m, 2H), 4.53 (m, 1H), 3.62 (m, 1H), 2.44 (m, 4H).

Step 5, N-O-bis(tert-butoxycarbonyl)-N-[cis-3-(4-fluorophenyl)cyclobutyl]hydroxylamine To a stirred solution of the trans-alcohol prepared in Step 4, above (33.5 g, 0.202 mol), $Ph_3P$ (60.85, g 0.232 mol) and N,O-bis-tert-butoxycarbonyl)hydroxylamine (54.06 g, 0.232 mol) in THF (200 ml) was added DEAD (36.5 mol, 0.232 mol) in THF (70 ml) at room temperature under an atmosphere of $N_2$ (exothermic). After stirring for 1.5 hours, volatiles were removed under reduced pressure. A mixture of $Et_2O$ (200 ml) and n-hexane (100 ml) was added to the resultant oil, insolubles were filtered off, and the filtrate was concentrated in vacuo. This treatment was repeated to afford 123 g of crude title compound as a yellow oil, which was purified by flash chromatography ($SiO_2$, 1.2 Kg, eluted with n-hexane/ethyl acetate (15:1) to afford 64.33 g (83.8% yield) of the title compound.

$^1$H NMR ($CDCl_3$) δ7.18 (m, 2H), 6.98 (m, 2H), 4.59 (m, 1H), 3.12 (m, 1H), 2.63 (m, 4H), 1.55 (s, 9H), 1.48 (s, 9H).

Step 6, N-[cis-3-(4-fluorophenyl)cyclobutyl]-N-hydroxyurea

To a stirred solution of the compound prepared in Step 5, above (64.3 g, 0.164 mol), in $CH_2Cl_2$ (330 ml) was added trifluoroacetic acid (81.4 ml) dropwise at 5° C. After stirring for 4 hours, the volatiles were removed in vacuo. Saturated aqueous $NaHCO_3$ (300 ml) was added and the whole extracted with ethyl acetate (2×400 ml, 1×200 ml). The organic layer was washed with water (200 ml) and brine (400 ml), then was dried over $MgSO_4$ and evaporated in vacuo to afford 27.0 g (90.8% yield) of the corresponding hydroxylamine. To a stirred solution of this hydroxylamine (27.0 g, 0.149 mol), i THF (300 ml) was added trimethylsilyl isocyanate (23.5 g, 0.203 mol) at room temperature under an atmosphere of $N_2$. After stirring overnight, MeOH (150 ml) was added to quench the reaction. Volatiles were removed in vacuo, and the resulting solid was recrystallized from i-PrOH. This provided 12.92 g (38.6% yield, first crop), 5.01 g (15.1% yield, second crop) and 0.76 g (2.3% yield, third crop) of the title compound as colorless plates. Total yield was 56.0%.

m.p. 155–157° C.

IR (nujol) v 3450, 3200, 1620, 1577, 1240, 1160, 830 $cm^{-1}$.

$^1$H NMR (DMSO-$d_6$) δ9.14 (s, 1H), 7.19 (m, 2H), 7.05 (m, 2H), 6.23 (s, 2H), 4.58 (m, 1H), 3.00 (m, 1H), 2.30 (m, 4H).

Example 52

N-[trans-3-(4-fluorophenyl)cyclobutyl]-N-hydroxyurea m.p. 134–136° C.

IR (nujol) v 3450, 3200, 1615, 1570, 1510, 1245, 1150, 830, 770 $cm^{-1}$.

$^1$H NMR ($CDCl_2$/DMSO-$d_6$) δ9.22 (s, 1H), 7.25 (t, J=8.8 Hz, 2H), 6.98 (t, J=8.8 Hz, 2H), 5.85 (s, 2H), 4.98 (m, 1H), 3.43 (m, 1H), 2.87 (m, 2H), 2.28 (m, 2H).

Example 53

N-[cis-3-(3-chlorophenyl)cyclobutyl]-N-hydroxyurea m.p. 157–158° C. (dec.)

IR (nujol) v 3450, 3340, 1645, 1570, 1155, 1090, 870, 860, 785, 690 $cm^{-1}$.

$^1$H NMR (DMSO-$d_6$) δ9.24 (s, 1H), 7.35 (m, 4H), 6.35 (s, 2H), 4.70 (m, 1H), 3.15 (m, 1H), 2.38 (m, 4H),

Example 54

N-[trans-3-(3-chlorophenyl)cyclobutyl]-N-hydroxylurea m.p. 127–128° C.

IR (nujol) v 3430, 1640, 1585, 1205, 1165, 1090, 1070, 920, 870, 770, 690 $cm^{-1}$.

$^1$H NMR (DMSO-$d_6$) δ9.14 (s, 1H), 7.26–7.13 (m, 4H), 5.51 (br s, 2H). 5.02 (m, 1H), 3.44 (m, 1H), 2.87 (m, 2H), 2.31 (m, 2H).

Example 55

N-[cis-3-(4-chlorophenyl)cyclobutyl]-N-hydroxyurea m.p. 155–157° C. (dec.).

IR (nujol) v 3450, 3200, 1618, 1577, 820 $cm^{-1}$.

$^1$H NMR (DMSO-$d_6$) δ9.02 (s, 1H), 7.17 (dd, J=8.4 Hz, 2H), 7.26 (d, J=8.4 Hz, 2H), 6.11 (s, 2H), 4.46 (dt, J=8.1 Hz, 1H), 2.89 (dt, J=8.1 Hz, 1H), 2.15 (m, 4H).

Example 56

N-[trans-3-(4-chlorophenyl)cyclobutyl]-N-hydroxyurea m.p. 147–148° C.

IR (nujol) v 1645, 1570, 1240, 1195, 1095, 820, 770 $cm^{-1}$.

$^1$H NMR (DMSO-$d_6$) δ9.07 (s, 1H), 7.14 (d, J=8.8 Hz, 4H), 6.13 (s, 2H), 4.59 (m, 1H), 3.15 (m, 1H), 2.46 (m, 2H), 1.93 (m, 2H).

Example 37

N-[trans-3-(4-bromophenyl)cyclobutyl]-N-hydroxyurea m.p. 162–164° C. (dec.).

IR (nujol) v 2900, 1640, 1565, 1460, 1380, 815 $cm^{-1}$.

$^1$H NMR (DMSO-$d_6$) δ9.27 (s, 1H), 7.48 (d, J=8.4 Hz, 2H), 7.26 (d, J=8.4 Hz, 2H), 6.33 (s, 2H), 4.78 (m, 1H), 3.40 (m, 1H), 2.69 (m, 2H), 2.14 (m, 2H).

Example 58

N-[cis-3-(4-bromophenyl)cyclobutyl]-N-hydroxyurea m.p. 164.5–166° C.

IR (nujol) v 3460, 1640, 1570, 1195, 810, 770 $cm^{-1}$.

$^1$H NMR (DMSO-$d_6$) δ9.19 (s, 1H), 7.48 (d, J=8.4 Hz, 2H), 7.19 (d, J=8.4 Hz, 2H), 6.29 (s, 2H), 4.64 (m, 1H), 3.06 (m, 1H), 2.33 (m, 4H).

Example 59

N-hydroxy-N-[trans-3-(4-trifluoromethylphenyl)cyclobutyl]urea m.p. 157.5–159.5° C.

IR (nujol) v 3470, 3180, 1645, 1570, 1330, 1160, 1120, 1070, 850, 830, 770 $cm^{-1}$.

$^1$H NMR (DMSO-$d_6$) δ9.31 (s, 1H), 7.68 (d, J=8.1 Hz, 2H), 7.54 (d, J=8.1 Hz, 2H), 6.35 (s, 2H), 4.83 (m, 1H), 3.49 (m, 1H), 2.76 (m, 2H), 2.20 (m, 2H).

Example 60

N-hydroxy-N-[cis-3-(4-trifluoromethylphenyl)cyclobutyl]urea m.p. 151–153° C.

IR (nujol) v 3530, 3150, 1630, 1580, 1330, 1170, 1120, 1070, 835 cm$^{-1}$.

$^1$H NMR (DMSO-d$_6$) δ9.21 (s, 1H), 7.68 (d, J=8.1 Hz, 2), 7.54 (d, J=8.1 Hz, 2H), 6.31 (s, 2H), 4.70(m, 1H), 3.09 (m, 1H), 2.38 (m, 4H).

Example 61

N-hydroxy-N-[trans-3-(4-methoxyphenyl)cyclobutyl]urea m.p. 139–139.5° C. (dec.)

IR (nujol) v 1615, 1570, 1515, 1465, 1250, 1030 cm$^{-1}$.

$^1$H NMR (DMSO-d$_6$) δ9.24 (s, 1H), 7.21 (d, J=8.4 Hz, 2H), 6.87 (d, J=8.4 Hz, 2H), 6.31 (s, 2H), 4.77 (m, 1H), 3.73 (s, 3H), 3.30 (m, 1H), 2.67 (m, 2H), 2.10 (m, 2H).

Example 62

N-Hydroxy-N-[cis-3-(α-styryl)cyclobutyl]urea m.p. 183.5–184.5° C.

IR (nujol) v 3460, 3180, 1610, 1580, 1190, 1090, 960, 745 cm$^{-1}$.

$^1$H NMR (DMSO-d$_6$) δ9.12 (s, 1H), 7.30 (m, 6H), 6.32 (s, 2H), 6.30 (d, J=17.6 Hz, 1H), 4.57 (m, 1H), 2.67 (m, 1H), 2.18 (m, 4H).

Example 63

N-hydroxy-N-[cis-3-(3-phenoxyphenyl)cyclobutyl]urea m.p. 127–129° C.

IR (nujol) v 3450, 3200, 1640, 1580, 1490, 1380, 1250, 750 cm$^{-1}$.

$^1$H NMR (DMSO-d$_6$) δ9.16 (s, 1H), 7.40–6.70 (m, 9H), 6.27 (s, 2H), 4.63 (m, 1H), 3.10 (m, 1H), 2.32 (m, 4H).

Example 64

N-([cis-3-(4-chlorophenyl)cyclobutyl]methyl)-N-hydroxyurea

Step 1, ethyl 3-(4-chlorophenyl)-cis-3-hydroxycyclobutanecarboxylate

The title compound was obtained from ethyl 3-oxocyclobutanecarboxylate (3.10 g, 22 mmol) and 4-chlorophenylmagnesium bromide (23 mmol) according to the procedure of Caputo et al., *J. Org. Chem.*, 33, 1959 (1968). Column chromatography (SiO$_2$, 300 g, 12.5% ethyl acetate in n-hexane) yielded the title compound (4.03 g, 72% yield).

$^1$H NMR (CDCl$_3$) δ7.44 (d, J=8.43 Hz, 2H), 7.35 (d, J=8.43 Hz, 2H), 4.21 (q, J=6.96 Hz, 2H), 3.25 (br s, 1H), 2.88–2.80 (m, 3H), 2.66–2.59 (m, 2H), 1.30 (t, J=6.96 Hz, 3H).

Step 2, ethyl cis 3-(4-chlorophenyl)cyclobutanecarboxylate

This compound was obtained from ethyl 3-(4-chlorophenyl)-cis-3-hydroxycyclobutanecarboxylate (1.42 g, 4.84 mmol) according to the procedure of Caputo et al. Column chromatography (SiO$_2$, 200 g, 5% ethyl acetate in n-hexane) yielded the title compound (0.47 g, 41% yield).

$^1$H NMR (CDCl$_2$) δ7.26 (d, J=8.43 Hz, 2H), 7.16 (d, J=8.43 Hz, 2H), 4.15 (q, J=6.96 Hz, 2H), 3.45–3.37 (m, 1H), 3.14–3.02 (m, 1H), 2.66–2.55 (m, 2H), 2.43–2.30 (m, 2H), 1.27 (t, J=6.96 Hz, 3H).

Step 3, [cis-3-(4-chlorophenyl)cyclobutyl]methanol

The carboxylate prepared in Step 2, above (0.52 g, 2.2 mmol), was converted to the title compound according to the procedure described in Example 67, Step 3.

$^1$H NMR (CDCl$_3$) δ7.25 (d, J=8.43 Hz, 2H), 7.13 (d, J=8.43 Hz, 2H), 3.61 (d, J=6.59 Hz, 2H), 3.47–3.36 (m, 1H), 2.56–2.39 (m, 3H), 1.93–1.80 (m, 2H).

Step 4, N,O-di-tert-butoxycarbonyl-N-([cis-3-(4-chlorophenyl)cyclobutyl]methyl)hydroxylamine The methanol prepared in Step 3, above (0.40 g, 2.0 mmol), was converted to the title compound (1.99 g, 99% yield) according to the procedure described in Example 15, Step 1.

$^1$H NMR (CDCl$_3$) δ7.25 (d, J=8.43 Hz, 2H), 7.11 (d, J=8.43 Hz, 2H), 3.61 (d, J=6.59 Hz, 2H), 3.37–3.31 (m, 1H), 2.64–2.43 (m, 3H), 1.89–1.77 (m, 2H), 1.53 (s, 9H), 1.48 (s, 9H).

Step 5, N-([cis-3-(4-chlorophenyl)cyclobutyl]methyl)-N-hydroxyurea

The hydroxylamine prepared in Step 4, above (0.82 g, 1.99 mmol), was converted to the title compound according to the procedure described in Example 15, Step 2. The crude product was recrystallized from 30% ethyl acetate in diisopropyl ether to afford the title compound (0.37 g. 73% yield), m.p. 127.5–128° C.

IR (KBr) v 3505, 3350, 3180, 1646, 1633, 1567, 1490 cm$^{-1}$.

$^1$H NMR (DMSO-d$_6$) δ9.20 (s, 1H), 7.33 (d, J=8.43 Hz, 2H), 7.23 (d, J=8.43 Hz, 2H), 6.22 (br s, 2H), 3.37 (d, j=6.59 Hz, 2H), 3.35–3.28 (m, 1H), 2.51–2.34 (m, 3H), 1.81–1.70 (m, 2H).

Anal. Calc. for C$_{12}$H$_{15}$ClN$_2$O$_2$; C, 56.59; H, 5.94; N, 11.00, Found: C, 56.96; H, 5.90; N, 10.99.

Example 65

N-([cis-3-(4-fluorophenyl)cyclobutyl]methyl)-N-hydroxyurea

Step 1, [cis-3-(4-fluorophenyl)cyclobutyl]methanol

Ethyl cis-3-(4-fluorophenyl)cyclobutanecarboxylate (3.31 g, 14.9 mmol) was converted according to the procedure of Escale et al., *Eur. J. Med. Chem.*, 13, 449 (1978) to the title compound (2.53 g, 94% yield).

$^1$H NMR (CDCl$_3$) δ7.20–7.11 (m, 2H), 7.02–6.94 (m, 2H), 3.61 (d, J=6.59 Hz, 2H), 3.43–3.35 (m, 1H), 2.54–2.40 (m, 3H), 1.90–1.79 (m, 2H).

Step 2, N,O-di-tert-butoxycarbonyl-N-([cis-3-(4-fluorophenyl)-1-cyclobutyl]methyl)hydroxylamine The compound prepared in Step 1, above (2.53 g, 14 mmol), was converted to the title compound (5.54 g, quant, yield) according to the procedure described in Example 15, Step 1.

$^1$H NMR (CDCl$_3$) δ7.16–7.10 (m, 2H), 7.01–6.92 (m, 2H0, 3.62 (d, J=6.59 Hz, 2H), 3.39–3.32 (m, 1H) 2.63–2.43 (m, 3H), 1.89–1.77 (m, 2H), 1.52 (s, 9H), 1.48 (s, 9H).

Step 3, N-([cis-3-(4-fluorophenyl)cyclobutyl]methyl)-N-hydroxyurea

The hydroxylamine prepared in Step 2 above (5.54 g, 14 mmol) was converted to the title compound according to the procedure described in Example 15, Step 2. The crude product was recrystallized from diisopropyl ether to afford the title compound (1.40 g, 42% yield), m.p. 102–103° C.

IR (KBr) v 3475, 3185, 2930, 1621, 1566, 1508, 1466 cm$^{-1}$.

$^1$H NMR (DMSO-d$_6$) δ9.21 (s, 1H), 7.27–7.21 (m, 2H), 7.14–7.06 (m, 2H), 6.22 (br s, 2H), 3.37 (d, J=6.59 Hz, 2H), 3.34–3.27 (m, 1H), 2.54–2.34 (m, 3H), 1.82–1.70 (m, 2H).

Anal. Calc. for C$_{12}$H$_{15}$FN$_2$O$_2$: C, 60.49; H, 6.35; N, 11.76. Found: C, 60.60; H, 6.58; N, 11.76.

Example 66

N-hydroxy-N-[(cis-3-phenylcyclobutyl)methyl]urea

Step 1, N,O-di-tert-butoxycarbonyl-N-[(cis-3-phenylcyclobutyl)methyl]hydroxylamine This compound was obtained from (cis-3-phenylcyclobutyl)methanol (0.49 g, 3.0 mmol) according to the procedure described in Example 15, Step 1 (1.00 g, 88% yield).

$^1$H NMR (CDCl$_3$) δ7.21–7.25 (m, 2H), 7.21–7.14 (m, 3H), 3.62 (d, J=6.59 Hz, 2H0, 3.43–3.36 (m, 1H), 2.62–2.45 (m, 3H), 1.93–1.81 (m, 2H), 1.53 (s, 9H), 1.48 (s, 9H).

Step 2, N-hydroxy-N-[(cis-3-phenylcyclobutyl)methyl]urea

The hydroxylamine prepared in Step 1, above (1.00 g, 2.6 mmol), was converted to the title compound according to the procedure described in Example 15. Step 2. The crude product was recrystallized from diisopropyl ether to afford the title compound (0.27 g, 47% yield), m.p. 100–100.5° C.

IR (KBr) v 3475, 3185, 1624, 1569, 1492, 1466 cm$^{-1}$.

$^1$H NMR (DMSO-d$_6$) δ 9.18 (s, 1H), 7.32–7.13 (m, 5H), 6.23 (br s, 2H), 3.38 (d, J=6.59 Hz, 2H), 3.33–3.25 (m, 1H), 2.56–2.34 (m, 3H), 1.84–1.72 (m, 2H).

Anal. Calc. for C$_{12}$H$_{16}$N$_2$O$_2$: C, 65.43; H, 7.32; N, 12.72. Found: C, 65.64; H, 7.39; N, 12.65.

Example 67

N-hydroxy-N-([cis-3-(4-trifluoromethylphenyl)cyclobutyl]methyl)urea

Step 1, methyl cis-3-hydroxyl-3-(4-trifluoromethylphenyl)cyclobutanecarboxylate

This compound was obtained from methyl 3-oxocyclobutanecarboxylate (2.56 g, 20 mmol) and 4-trifluoromethylphenylmagnesium bromide (20 mmol) according to the procedure of Caputo et al. Column chromatography (SiO$_2$, 200 g, 30% ethyl acetate in n-hexane) yielded the title compound (3.21 g, 58% yield).

$^1$H NMR (CDCl$_3$) δ 7.64 (d, J=8.43 Hz, 2H), 7.62 (d, J=8.43 Hz, 2H), 3.77 (s, 3H), 3.00–2.84 (m, 3H), 2.71–2.59 (m, 2H).

Step 2, methyl cis-3-(4-trifluoromethylphenyl)cyclobutanecarboxylate

This compound was obtained from the product of Step 1 (3.21 g, 11.7 mmol) according to the procedure of Caputo et al. Column chromatography (SiO$_2$, 200 g, 10% diethyl ether in n-hexane) yielded the title compound (2.63 g, 87% yield).

$^1$H NMR (CDCl$_3$) δ 7.56 (d, J=8.43 Hz, 2H), 7.34 (d, J=8.43 Hz, 2H), 3.70 (s, 3H), 3.55–3.47 (m, 1H), 3.20–3.09 (m, 1H), 2.71–2.60 (m, 2H), 2.50–2.36 (m, 2H).

Step 3, [cis-3-(4-trifluoromethylphenyl)cyclobutyl]methanol

A solution of the compound prepared in Step 2, above (1.29 g, 5 mmol) in diethyl ether (100 ml) was added dropwise to a stirred suspension of LiAlH$_4$ (0.23 g, 6 mmol) in diethyl ether (20 ml) over 30 minutes at room temperature under a nitrogen atmosphere. The reaction mixture was stirred for 3 hours, cooled to 0° C., and excess hydride was destroyed by addition of water (2.5 ml). To the resultant mixture was added 20% aqueous sulfuric acid (20 ml) and the organic phase was separated. The aqueous phase was extracted with diethyl ether (2×20 ml), and the combined extracts were washed with water (20 ml), saturated aqueous sodium bicarbonate (20 ml) and brine (20 ml), then dried over MgSO$_4$. Evaporation of the solvent gave a clear colorless liquid (quantitative yield) which was used without further purification.

$^1$H NMR (CDCl$_3$) δ 7.54 (d, J=8.43 Hz, 2H), 7.33 (d, J=8.43 Hz, 2H), 3.63 (t, J=6.59 Hz, 2H), 3.55–3.45 (m, 1H), 2.66–2.44 (m, 3H), 1.99–1.86 (m, 2H), 1.32 (t, J=5.13 Hz, 1H).

Step 4, N,O-di-tert-butoxycarbonyl-N-([cis-3-(4-trifluoromethylphenyl)cyclobutyl]methyl)hydroxylamine The compound prepared in Step 3, above (0.69 g, 5 mmol), was converted to the title compound (1.80 g, 68% yield) according to the procedure described in Example 15 Step 1.

$^1$H NMR (CDCl$_3$) δ 7.57 (d, J=8.43 Hz, 2H), 7.29 (d, J=8.43 Hz, 2H), 3.62 (d, J=6.59 Hz, 2H), 3.48–3.41 (m, 1H), 2.68–2.48 (m, 3H), 1.95–1.82 (m, 2H), 1.53 (s, 9H), 1.48 (s, 9H).

Step 5, N-hydroxy-N-([cis-3-(4-trifluoromethylphenyl)cyclobutyl]methyl)urea

The hydroxylamine prepared in Step 4, above (1.51 g, 3.4 mmol), was converted to the title compound according to the procedure described in Example 15, Step 2. The crude product was recrystallized from diethyl ether/n-hexane to afford the title compound (0.30 g, 31% yield), m.p. 144–146° C.

IR (KBr) v 3510, 3195, 1649, 1577, 1475, 1459 cm$^{-1}$.

$^1$H NMR (DMSO-d$_6$) δ 9.16 (s, 1H), 7.64 (d, J=8.43 Hz, 2H), 7.43 (d, J=8.43 Hz, 2H), 6.23 (br s, 2H), 3.47–3.38 (m, 1H), 3.37 (d, J=6.59 Hz, 2H), 2.58–2.38 (m, 3H), 1.88–1.76 (m, 2H).

Anal. Calc. for C$_{13}$H$_{15}$F$_3$N$_2$O$_2$: C, 54.17; H, 5.24; N, 9.72. Found: C, 54.12; H, 5.28; N, 9.66.

Example 68

N-hydroxy-N-(1-[cis-3-(4-trifluoromethylphenyl)cyclobutyl]ethyl)urea

Ethyl 3-(4-trifluoromethylphenyl)cyclobutanecarboxylic acid (1.85 g, 6.8 mmol) was dissolved in EtOH (70 ml) and refluxed for 4 hours with an excess of aqueous KOH (0.56 g in 30 ml H$_2$O). The volatiles were removed under reduced pressure and the residue was extracted with Et$_2$O to remove nonacidic impurities. The aqueous layer was then acidified with 2N aqueous HCl and extracted with CHCl$_3$. The combined extracts were washed with H$_2$O, dried over MgSO$_4$ and concentrated in vacuo to give 1.47 g of the corresponding carboxylic acid as white crystals.

To a cooled (0° C.) solution of the carboxylic acid (1.45 g, 6.0 mmol) thus prepared, in dry Et$_2$O (20 ml), was added dropwise a 1.10 M solution of methyllithium in dry Et$_2$O (10.9 ml, 12.0 mmol) under an argon atmosphere, and the mixture was stirred overnight at room temperature. The reaction was quenched by addition of saturated aqueous NH$_4$Cl and extracted with Et$_2$O. The combined organic layers were washed with H$_2$O and brine, dried over MgSO$_4$ and concentrated in vacuo to give 1.24 g of the corresponding methyl ketone as a colorless oil.

To a cooled (0° C.) solution of the ketone (1.24 g, 5.1 mmol) thus prepared, in MeOH (30 ml) was added NaBH$_4$ (0.39 g, 10 mmol) in small portions over 10 minutes. The reaction mixture was stirred for 2 hours at room temperature and then the volatiles were removed under reduced pressure. The residue was diluted with H$_2$O and extracted with ethyl acetate. The organic layer was dried over MgSO$_4$ and concentrated in vacuo. After chromatographic purification (SiO$_2$, 100 g, eluted with hexane/ethyl acetate, 5:1), 0.96 g (78% yield) of the corresponding alcohol was obtained as a colorless oil.

$^1$H NMR (CDCl$_3$) δ 7.54 (d, J=8.1 Hz, 2H), 7.30 (d, J=8.1 Hz, 2H), 3.77–3.57 (m, 1H), 3.45–3.28 (m, 1H), 2.56–2.22 (m, 3H), 2.05–1.80 (m, 2H), 1.40 (br s, 1H), 1.13 (d, J=6.2 Hz, 3H).

The alcohol thus prepared was converted into the title compound, m.p. 146.9–147.8° C., according to the procedure described in Example 67.

IR (KBr) v 3460, 1670, 1460, 1330, 1270, 1240, 1170 cm$^{-1}$.

$^1$H NMR (CDCl$_3$) δ 8.83 (s, 1H), 7.64 (d, J=7.7 Hz, 2H), 7.42 (d, J=8.1 Hz, 2H), 6.22 (s, 2H), 4.11–3.94 (m, 1H), 3.40–3.25 (m, 1H), 2.50–2.33 (m, 3H), 1.84–1.72 (m, 2H), 0.93 (d, J=6.6 Hz, 3H).

Example 69

N-hydroxy-N-[cis-3-(4-fluorophenyl)cyclobutyl] thiourea

To a stirred solution of cis-3-(4-fluorophenyl)cyclobutylhydroxylamine (1.81 g, 10 mmol) in THF (30 ml) was added trimethylsilylisothiocyanate (1.58 g, 12 mmol) at room temperature. After stirring for 3 hours at 70° C., MeOH (20 ml) was added. Volatiles were removed in vacuo, and the residue recrystallized from ethyl acetate/n-hexane/EtOH to afford 1.34 g (55.8% yield) of the title compound, m.p. 156–158° C.

IR (nujol) v 2850, 1620, 1610, 1510, 1490, 1350, 1220, 1110, 880, 835 cm$^{-1}$.

$^1$H NMR (DMSO-d$_6$) δ 9.69 (s, 1H), 7.25 (m, 2H), 7.00 (m, 4H), 5.80 (m, 1H), 3.12 (m, 1H), 2.48 (m, 4H).

Example 70 ethyl-N'-[cis-3-(4-fluorophenyl)cyclobutyl]-N'-hydroxyhydantoate

To a stirred solution of cis-3-(4-fluorophenyl)cyclobutylhydroxylamine (0.9 g, 5 mmol) in THF (20 ml) was added ethyl isocyanatoacetate (0.71 g, 5.5 mmol). After stirring for 10 minutes, EtOH was added. Volatiles were removed in vacuo and the resulting residue was recrystallized from ethyl acetate/n-hexane to afford 1.10 g (71% yield) of the title compound as colorless needles, m.p. 130–132° C.

IR (nujol) v 3180, 1740, 1645, 1600, 1510, 1300, 1220, 1190, 1125, 830 cm$^{-1}$.

$^1$H NMR (DMSO-d$_6$) δ 7.25 (s, 1H), 7.19 (m, 2H), 6.97 (m, 2H), 6.46 (t, J=5.8 Hz, 1H), 4.77 (m, 1H), 4.20 (q, J=7.0 Hz, 2H), 3.99 (d, J=5.8 Hz, 2H), 3.08 (m, 1H), 2.47 (m, 4H), 1.28 (t, J=7.0 Hz, 3H).

Example 71

N-[cis-3-(4-fluorophenyl)cyclobutyl]-N-hydroxy-N'-p-toluenesulfonylurea

To a stirred solution of cis-3-(4-fluorophenyl)cyclobutylhydroxylamine (0.9 g, 3 mmol) in THF (20 ml) was added p-toluenesulfonyl isocyanate (1.085 g, 5.5 mmol) at room temperature. The resultant precipitates were collected by filtration and recrystallized from ethyl acetate/EtOH to provide 1.68 g (89% yield) of the title compound as a colorless solid, m.p. 177–178° C. (dec.).

IR (nujol) v 2950, 1640, 1515, 1350, 1170, 880, 830 cm$^{-1}$.

$^1$H NMR (DMSO-D$_6$) δ 9.68 (s, 1H), 7.79 (d, J=7.5 Hz, 2H), 7.37 (d, J=7.5 Hz, 2H), 7.16 (m, 5H), 4.58 (m, 1H), 3.32 (s, 3H), 3.08 (m, 1H), 2.35 (m, 4H).

Example 72

N'-[cis-3-(4-fluorophenyl)cyclobutyl]-N'-hydroxyhydantoic acid

To a stirred solution of the compound prepared in Example 71, above (1.03 g, 3.32 mmol), in a THF/MeOH (5 ml/5 ml) solution was added dropwise KOH (0.285 g, 4.32 mmol) in H$_2$O (7 ml). After stirring overnight, the volatiles were removed in vacuo, an Et$_2$O/H$_2$O (40 ml/30 ml) mixture was added, the aqueous layer was separated and acidified with 10% aqueous HCl and the whole was extracted with ethyl acetate (2×50 ml), washed with water and brine, then dried over MgSO$_4$ and evaporated in vacuo. The resulting solid was triturated with an Et$_2$O/n-hexane mixture to afford 0.74 g of desired product as a colorless solid, m.p. 137–139° C. (dec.).

IR (nujol) v 3100, 1715, 1625, 1540, 1510, 1235, 1115, 910, 830 cm$^{-1}$.

$^1$H NMR (DMSO-d$_6$) δ 9.34 (s, 1H), 7.19 (m, 5H), 4.61 (m, 1H), 3.65 (d, J=4 Hz, 2H), 3.05 (m, 1H), 2.30 (m, 4H).

Example 73

2-[cis-3-(4-fluorophenyl) cyclobutyl]-1,2,4-azoisoxazolizin-3,5-dione

To a stirred solution of cis-3-(4-fluorophenyl)cyclobutylhydroxylamine (0.09 g, 5 mmol) in THF (20 ml) was added N-(chlorocarbonyl)isocyanate (0.55 g, 5 mmol) at room temperature. After stirring for 30 minutes, volatiles were removed in vacuo and the resulting residue recrystallized from EtOH to afford 0.36 g (29% yield) of the desired product as colorless needles, m.p. 167–168.5° C. (dec.).

IR (nujol) v 1910, 1830, 1605, 1560, 1215, 1145, 990, 960, 840 cm$^{-1}$.

$^1$H NMR (DMSO-d$_6$) δ 12.45 (s, 1H), 7.22 (m, 4H), 4.56 (m, 1H), 3.25 (m, 1H), 2.62 (m, 2H), 2.31 (m, 2H).

Example 74

N-ethoxycarbonyloxy-N-[cis-3-(4-fluorophenyl) cyclobutyl]urea

To a stirred solution of the compound prepared in Example 51, above (0.448 g, 2 mmol), in CH$_2$Cl$_2$ (10 ml) was added triethylamine (0.223 g, 2.2 mmol) and ethyl chloroformate (0.24 g, 2.2 mmol) at room temperature. After stirring for 20 minutes, saturated aqueous NaCl was added and the whole was extracted with ethyl acetate (3×30 ml), the organic layer was washed with water (30 ml) and brine (30 ml), then dried over MgSO$_4$ and evaporated in vacuo. Recrystallization of the resulting residue from ethyl acetate provided 290 mg (49% yield) of the title compound as colorless plates m.p. 124–126° C.

IR (neat) v 3360, 1590, 1550, 1255, 1160, 1110, 750, 690 cm$^{-1}$.

$^1$H NMR (DMSO-d$_6$) δ 7.20 (m, 4H), 6.84 (s, 2H), 4.63 (m, 1H), 4.25 (q, J=6.9 Hz, 2H), 3.13 (m, 1H), 2.50 (br s, 4H), 1.27 (t, J=6.9 Hz, 3H).

Example 75

N-hydroxy-N-[cis-3-(4-phenoxyphenyl)cyclobutyl]urea m.p. 187–188° C.

IR (KBr) v 3450, 3200, 1620, 1580, 1510, 1260 cm$^{-1}$.

$^1$H NMR (DMSO-d$_6$) δ 9.18 (s, 1H), 7.40–7.33 (m, 2H), 7.26–7.22 (m, 2H), 7.11 (dddd, J=7.69, 7.69, 1.10, 1.10 Hz, 1H), 6.99–6.94 (m, 4H), 6.29 (s, 2H), 4.67–4.61 (m, 1H), 3.09–3.03 (m, 1H), 2.39–2.25 (m, 4H).

Example 76

N-hydroxy-N-[trans-3-(4-phenoxyphenyl)cyclobutyl]urea m.p. 163–165° C.

IR (KBr) v 3450, 1620, 1570, 1510, 1260 cm$^{-1}$.

$^1$H NMR (DMSO-d$_6$) δ 9.26 (s, 1H), 7.41–7.30 (m, 4H), 7.11 (dddd, J=7.51, 7.51, 1.10, 1.10 Hz, 1H), 7.01–6.94 (m, 4H), 6.32 (s, 2H), 4.83–4.77 (m, 1H), 3.41–3.34 (m, 1H), 2.75–2.64 (m, 2H), 2.20–2.11 (m, 2H).

Example 77

N-([cis-3-(2-benzofuryl)-3-methyl]cyclobutyl)-N-hydroxyurea m.p. 190–192° C. (dec.).

IR (KBr) v 3500, 3300, 1630, 1560, 1460 cm$^{-1}$.

$^1$H NMR (DMSO-d$_6$) δ 9.20 (s, 1H), 7.56–7.49 (m, 2H), 7.26–7.16 (m, 2H), 6.56 (d, J=1.1 Hz, 1H), 6.33 (s, 2H), 4.90–4.84 (m, 1H), 2.78–2.70 (m, 2H), 2.07 (ddd, J=8.42, 8.42, 2.56 Hz, 2H), 1.48 (s, 3H).

Example 78

N-([trans-3-(2-benzofuryl)-3-methyl]cyclobutyl)-N-hydroxyurea m.p. 160–162° C.

IR (KBr) v 3420, 2970, 1640, 1580, 1460 cm$^{-1}$.

$^1$H NMR (DMSO-d$_6$) δ 9.27 (s, 1H), 7.57–7.52 (m, 2H), 7.27–7.17 (m, 2H), 6.72 (d, J=0.74 Hz, 1H), 6.33 (s, 2H), 4.82–4.76 (m, 1H), 2.44–2.36 (m, 4H), 1.55 (s, 3H).

Example 79

N-[cis-3-(4-biphenyl)cyclobutyl]-N-hydroxyurea m.p. 205–207° C. (dec.).

IR (KBr) v 3450, 1620, 1570, 1470 cm$^{-1}$.

$^1$H NMR (DMSO-d$_6$) δ 9.23 (s, 1H), 7.65–7.58 (m, 4H), 7.47–7.42 (m, 2H), 7.36–7.31 (m, 3H), 6.29 (s, 2H), 4.70–4.64 (m, 1H), 3.28–3.08 (m, 1H), 2.36–2.33 (m, 4H).

Example 80

N-[trans-3-(4-biphenyl)cyclobutyl]-N-hydroxyurea m.p. 196–197° C. (dec.).

IR (KBr) v 3450, 1620, 1570 cm$^{-1}$.

$^1$H NMR (DMSO-d$_6$) δ 9.29 (s, 1H), 7.67–7.61 (m, 4H), 7.48–7.31 (m, 5H), 6.34 (s, 2H), 4.88–4.82 (m, 1H), 3.45–3.39 (m, 1H), 2.78–2.67 (m, 2H), 2.25–2.15 (m, 2H).

Example 81

N-[cis-3-(3,4-difluorophenyl)cyclobutyl]-N-hydroxyurea m.p. 154–155° C.

IR (KBr) v 3500, 3200, 1640, 1520, 1480 cm$^{-1}$.

$^1$H NMR (DMSO-d$_6$) δ 9.22 (s, 1H), 7.40–7.20 (m, 2H), 7.08–7.05 (m, 1H), 6.30 (s, 2H), 4.66–4.59 (m, 1H), 3.18–3.05 (m, 1H), 2.43–2.21 (m, 4H).

Example 82

N-[trans-3-(3,4-difluorophenyl)cyclobutyl]-N-hydroxyurea m.p. 124–126° C.

IR (KBr) v 3500, 1650, 1570, 1520 cm$^{-1}$.

$^1$H NMR (DMSO-d$_6$) δ 9.30 (s, 1H), 7.40–7.30 (m, 2H), 7.18–7.10 (m, 1H), 6.33 (s, 2H), 4.80–4.74 (m, 1H), 3.48–3.18 (m, 1H), 2.72–2.61 (m, 2H), 2.21–2.11 (m, 2H).

Example 83

N-hydroxy-N-[cis-3-(4-methylphenyl)cyclobutyl]urea m.p. 177–179° C.

IR (KBr) v 3470, 3200, 1620, 1570, 1460 cm$^{-1}$.

$^1$H NMR (DMSO-d$_6$) δ 9.16 (s, 1H), 7.10 (s, 4H), 6.25 (s, 2H), 4.65–4.59 (s, 1H), 3.04–2.98 (m, 1H), 2.39–2.22 (m, 7H).

Example 84

N-hydroxy-N-[trans-3-(4-methylphenyl)cyclobutyl]urea m.p. 165–166° C.

IR (KBr) v 3480, 1650, 1570, 1430 cm$^{-1}$.

$^1$H NMR (DMSO-d$_6$) δ 9.24 (s, 1H), 7.20–7.10 (m, 4H), 6.30 (s, 2H), 4.82–4.76 (m, 1H), 3.41–3.27 (m, 1H), 2.73–2.62 (m, 2H), 2.27 (s, 3H), 2.16–2.07 (m, 2H).

Example 85

N-[cis-3-(2-fluorophenyl)cyclobutyl]-N-hydroxyurea m.p. 154–156° C.

IR (KBr) v 3500, 3300, 3200, 1660, 1640, 1570, 1490, 1450 cm$^{-1}$.

$^1$H NMR (DMSO-d$_6$) δ 9.16 (s, 1H), 7.34–7.07 (m, 4H), 6.29 (s, 2H), 4.72–4.66 (m, 1H), 3.32–3.22 (m, 1H), 2.39–2.31 (m, 4H).

Example 86

N-[trans-3-(4-tert-butylphenyl)cyclobutyl]-N-hydroxyurea m.p. 157–158° C.

IR (KBr) v 3500, 3200, 2950, 1640, 1580, 1340 cm$^{-1}$.

$^1$H NMR (DMSO-d$_6$) δ 9.25 (s, 1H), 7.35–7.20 (m, 4H), 6.31 (s, 2H), 4.82–4.76 (m, 1H), 3.40–3.26 (m, 1H), 2.73–2.62 (m, 2H), 2.18–2.09 (m, 2H), 1.27 (s, 9H).

Example 87

N-[cis-3-(4-tert-butylphenyl)cyclobutyl]-N-hydroxyurea m.p. 165° C. (dec.).

IR (KBr) v 3500, 3300, 2950, 2800, 1635, 1560, 1450 cm$^{-1}$.

$^1$H NMR (DMSO-d$_6$) δ 9.17 (s, 1H), 7.32–7.13 (m, 4H), 6.28 (s, 2H), 4.70–4.57 (m, 1H), 3.05–2.95 (m, 1H), 2.39–2.24 (m, 4H), 1.26 (s, 9H).

Example 88

N-[cis-3-(4-tert-butylphenyl)cyclobutyl]-N-hydroxythiourea m.p. 165–167° C. (dec.).

IR (KBr) ν 3280, 1600, 1490 cm$^{-1}$.

$^1$H NMR (DMSO-d$_6$) δ 9.77 (s, 1H), 7.56–7.14 (m, 4H), 6.26 (s, 2H), 5.77–5.67 (m, 1H), 3.09–2.99 (m, 1H), 2.51–2.28 (m, 4H), 1.26 (s, 9H).

Example 89

N-[(cis-3-benzyloxycyclobutyl)methyl]-N-hyroxyurea m.p. 92.6–92.8° C.

IR (KBr) ν 3460, 1620, 1575, 1500, 1460, 1150, 1090 cm$^{-1}$.

$^1$H NMR (DMSO-d$_6$) δ 9.15 (s, 1H), 7.39–7.25 (m, 5H), 6.21 (s, 2H), 4.34 (s, 2H), 3.90–3.34 (m, 1H), 3.40–3.26 (m, 2H), 2.35–2.21 (m, 2H), 2.11–1.94 (m, 1H), 1.64–1.51 (m, 2H).

Example 90

N-[(trans-3-benzyloxycyclobutyl)methyl]-N-hydroxyurea m.p. 100.6–101.5° C.

IR (KBr) ν 3460, 2900, 1680, 1580, 1500, 1165, 1130 cm$^{-1}$.

$^1$H NMR (DMSO-d$_6$) δ 9.19 (s, 1H), 7.39–7.25 (m, 5H), 6.21 (s, 2H), 4.34 (s, 2H), 4.18–4.04 (m, 1H), 3.40–3.27 (m, 2H), 2.51–2.39 (m, 1H), 2.09–1.90 (m, 4H).

Example 91

N-(cis-3-cyclohexylcyclobutyl)-N-hydroxyurea m.p. 161–162° C.

IR (KBr) ν 3490, 3350, 3220, 2930, 2855, 1605, 1585, 1458 cm$^{-1}$.

$^1$H NMR (DMSO-d$_6$) δ 9.03 (s, 1H), 6.20 (br s, 2H), 4.50–4.37 (m, 1H), 2.03–1.92 (m, 2H), 1.89–1.75 (m, 2H), 1.71–1.40 (m, 6H), 1.25–0.99 (m, 4H), 0.82–0.67 (m, 2H).

Example 92

N-[cis-3-(3-cyclohexenyl)cyclobutyl]-N-hydroxyurea m.p. 154–155° C.

IR (KBr) 3500, 3350, 1610, 1460 cm$^{-1}$.

$^1$H NMR (DMSO-d$_6$) δ 9.02 (s, 1H), 6.19 (s, 2H), 5.63 (s, 2H), 4.49–4.42 (m, 1H), 2.03–1.80 (m, 8H), 1.64–1.46 (m, 2H), 1.40–1.27 (m, 2H), 1.12–1.00 (m, 1H).

Example 93

N-hydroxy-N-(1-[3-(4-trifluoromethylphenyl)cyclobutyl]ethyl)urea

Trans:cis=2:1.

m.p. 137.2–137.8° C.

IR (KBr) ν 3460, 1670, 1575, 1480, 1330, 1130, 1070 cm$^{-1}$.

$^1$H NMR (DMSO-d$_6$) δ 8.82 (s) and 8.79 (s, 1H), 7.66 (d, J=8.1 Hz) and 7.63 (d, J=7.9 Hz, 2H), 7.49 (d, J=8.4 Hz) and 7.42 (d, J=8.4 Hz, 2H), 6.22 (s, 2H), 4.34–4.20 (m) and 4.07–3.95 (m, 1H), 3.65–3.49 (m) and 3.40–3.25 (m, 1H), 2.50–2.33 (m) and 2.29–2.03 (m) and 1.83–1.71 (m, 5H), 0.97 (d, J=6.6 Hz) and 0.92 (d, J=6.6 Hz, 3H).

Example 94

N-hydroxy-N-([3-(4-trifluoromethylphenyl)cyclobutyl]methyl)urea

Trans:cis=6:1.

m.p. 127.8–128.7° C.

IR (KBr) ν 3500, 3350, 1640, 1570, 1500, 1470, 1330, 1165, 1120, 1070 cm$^{-1}$.

$^1$H NMR (DMSO-d$_6$) δ 9.23 (s, 1H), 7.65 (d, J=8.0 Hz, 2H), 7.48 (d, J=8.4 Hz, 2H), 6.24 (s, 2H), 3.73–3.57 (m, 1H), 3.40–3.26 (m, 2H), 2.64–2.51 (m, 1H), 2.25–2.08 (m, 4H).

Example 95

N-[cis-3-(3-fluorophenyl)cyclobutyl]-N-hydroxyurea m.p. 152–153° C.

IR (KBr) ν 3465, 3340, 3200, 1616, 1589, 1572, 1470 cm$^{-1}$.

$^1$H NMR (DMSO-d$_6$) δ 9.21 (s, 1H), 7.39–7.30 (m, 1H), 7.09–6.96 (m, 3H), 6.32 (br s, 2H), 4.73–4.59 (m, 1H), 3.18–3.04 (m, 1H), 2.45–2.25 (m, 4H).

Example 96

N-(cis-3-benzylcyclobutyl)-N-hydroxyurea m.p. 169–170° C.

IR (KBr) ν 3455, 3335, 3190, 1615, 1571, 1474 cm$^{-1}$.

$^1$H NMR (DMSO-d$_6$) δ 9.11 (s, 1H), 7.30–7.13 (m, 5H), 6.22 (br s, 2H), 4.52–4.41 (m, 1H), 2.62 (d, J=6.59 Hz, 2H), 2.12–1.86 (m, 5H).

Example 97

N-hydroxy-N-[cis-3-(2-phenoxyphenyl)cyclobutyl]urea m.p. 155–157° C.

IR (KBr) 3500, 3350, 1660, 1580, 1485 cm$^{-1}$.

$^1$H NMR (DMSO-d$_6$) δ 9.13 (s, 1H), 7.40–7.12 (m, 5H), 7.09–7.03 (m, 1H), 6.90–6.83 (m, 3H), 6.26 (s, 2H), 4.60–4.53 (m, 1H), 3.19–3.12 (m, 1H), 2.32–2.22 (m, 4H).

Example 98

N-[3-(2-furyl)cyclobutylmethyl]-N-hydroxyurea

Step 1, ethyl-[3-(2-furyl)-3-hydroxy]cyclobutanecarboxylate

A solution of furan (1.67 ml, 23 mmol) in THF (20 ml) was cooled to −78° C. and treated with n-butyllithium (1.55 M in hexane, 14.8 ml, 23 mmol). The resulting solution was allowed to warm to between −10 and 0° C. and was held at that temperature for 1 hour. The mixture was then cooled to −78° C. and added to a stirred solution of ethyl-3-oxocyclobutane carboxylate (3.0 g, 21 mmol) in THF (30 ml) at −78° C. After being stirred at −78° C. for 0.5 hours, the mixture was quenched with aqueous ammonium chloride and the product was extracted with ether and dried over magnesium sulfate. Removal of solvent gave an oil, which was purified on a column of silica gel with EtOAc/n-hexane (1:5), affording the title compound (1.39 g, 31.5% yield) as a colorless oil.

Step 2, ethyl-3-(2-furyl)cyclobutane carboxylate

A stirred suspension of diphosphorus tetraiodide (2.50 g, 4.4 mmol) in dry benzene (40 ml) was heated for several minutes under nitrogen to yield an orange colored solution, to which a solution of the compound prepared in Step 1, above (1.54 g, 7.30 mmol) in dry benzene (20 ml) was added in one portion. The resulting mixture was heated at 80° C. for 15 minutes and then quenched with aqueous sodium bicarbonate. The organic phase was extracted with ether and the extract was washed with aqueous sodium sulfite, water and brine. The organic phase was dried over sodium sulfate. Removal of solvent gave the title compound (1.42 g, 99.8% yield) as a yellow oil.

Step 3, N-[3-(2-furyl)cyclobutylmethyl]-N-hydroxyurea

The compound prepared in Step 2, above, was converted to the title compound according to the procedure described in Example 15. The crude product was recrystallized from ethyl acetate/n-hexane to afford the title compound (199 mg, 12.5% yield), m.p. 89–100° C.

IR (KBR) v 3460, 3300, 1640, 1560, 1510 cm$^{-1}$.

$^1$H NMR (DMSO-d$_6$) 9.19 (s, 0.4H), 9.16 (s, 0.6H), 7.52–7.49 (m, 1H), 6.36–6.32 (m, 1H), 6.21 (s, 1H), 6.16–6.08 (m, 1H), 3.48 (d, J=7.33 Hz, 0.8H), 3.36 (d, J=6.96 Hz, 1.2H), 3.49–3.29 (m, 1H), 2.37–2.27 (m, 2H), 2.17–2.06 (m, 1H), 1.89–1.78 (m, 2H).

Example 99

N-[trans-3-(3-fluorophenyl)cyclopentyl]-N-hydroxyurea

The title compound (after recrystallization from ethyl acetate/hexane) was prepared from cis-3-(3-fluorophenyl) cyclopentan-1-ol according to the procedure described in Example 100, m.p. 113.0–114.0° C.

IR (KBr) v 3500, 3200, 2950, 2850, 1640, 1580, 1450 cm$^{-1}$.

$^1$H NMR (DMSO-d$_6$) δ9.12 (s, 1H), 7.34 (m, 1H), 7.13 (m, 3H), 6.29 (br s, 2H), 4.74 (m, 1H), 3.17 (m, 1H), 2.06–1.72 (m, 5H), 1.51 (m, 1H).

Anal. Calc. for C$_{12}$H$_{15}$N$_2$O$_2$F: C, 60.49; H, 6.34; N, 11.76. Found: C, 60.31; H, 6.44; N, 11.82.

Example 100

N-[cis-3-(3-fluorophenyl)cyclopentyl]-N-hydroxyurea

Step 1, 3-(3-fluorophenyl)cyclopent-2-en-1-one 1-(3-Fluorophenyl)-1,4-pentanedione (23 g, 0.12 mmol) was dissolved in water (550 ml) containing 11 g of sodium hydroxide and the solution was stirred at 100° C. for 3 hours. After cooling to 0° C. the resultant brown crystals were collected by filtration and washed with water. The title compound (9 g, 45% yield) was obtained by recrystallization from hexane as a yellow solid.

$^1$H NMR (CDCl$_3$) δ 7.44 (m, 2H), 7.33 (m, 1H), 7.20 (m, 1H), 6.57 (m, 1H), 3.03 (m, 2H), 2.61 (m, 2H).

Step 2, 1-cis-(tert-butyldimethylsilyoxy)-3-(3-fluorophenyl)cyclopentane

To a mixture of the product of Step 1, above (0.82 g, 4.6 mmol), and cerium (III) chloride heptahydrate (1.7 g, 4.6 mmol) in MeOH (10 ml) was added NaBH$_4$ (0.17 g, 4.6 mmol) portionwise in solid form. The mixture was stirred for 10 minutes, quenched with ice cold water and then extracted with ethyl acetate (3×10 ml). The combined extracts were dried over MgSO$_4$ and solvent was removed in vacuo to yield 0.8 g of the corresponding allylic alcohol as a yellow solid. To a solution of the allylic acid (0.8 g) in anhydrous DMF (2 ml) was added successively imidazole (0.75 g, 10 mmol), and tert-butyldimethylsilylchloride (0.80 g, 5.5 mmol). The mixture was stirred at room temperature for 3 hours, water (10 ml) was added, and the reaction mixture was extracted with ethyl acetate and washed with 1N aqueous HCl, saturated aqueous NaHCO$_3$ and brine. The combined extracts were dried over MgSO$_4$ and concentrated to afford the corresponding silylated allylic alcohol as a brown oil.

A suspension of the silylated allylic alcohol, 5% Pd/C (0.2 g) and absolute EtOH (5 ml) was stirred under a hydrogen atmosphere for 18 hours and the catalyst was removed by filtration. The reaction mixture was concentrated under reduced pressure and purified by chromatography on silica gel (ethyl acetate/hexane, 1:9) to afford 1.8 g (80% yield) of the title compound as pale yellow oil.

$^1$H NMR (CDCl$_3$) δ 7.22 (m, 1H), 7.03 (m, 2H), 6.85 (m, 1H), 4.35 (m, 1H), 3.01 (m, 1H), 2.32 (m, 1H), 2.01 (m, 1H), 1.88–1.55 (m, 4H).

Step 3, cis-3-(3-fluorophenyl)cyclopentan-1-ol

A solution of the compound prepared in Step 2, above (9.4 g, 30 mmol), in THF (100 ml) was cooled to 0° C., and n-Bu$_4$NF (1 M solution in THF, 60 ml) was added. The reaction mixture was warmed to room temperature and stirred for 1 hour. The mixture was diluted with ethyl acetate, washed with brine, dried over MgSO$_4$ and concentrated in vacuo. Purification by column chromatography (ethyl acetate/hexane, 1:7) affording the title compound (4.5 g, 83% yield) as a clear oil.

$^1$H NMR (CDCl$_3$) δ 7.24 (m, 1H), 7.18 (m, 2H), 6.87 (m, 1H), 4.44 (m, 1H), 3.03 (m, 1H), 2.46 (m, 1H), 2.08–1.78 (m, 3H), 1.64 (m, 2H).

Step 4, 1-trans-benzoyloxy-3-(3-fluorophenyl) cyclopentane

To a solution of the compound prepared in Step 3, above (4.5 g, 25 mmol), and PPh$_3$ (7.2 g, 27.5 mmol) in THF (15 ml) was added successively benzoic acid (3.35 g, 27.5 mmol in 10 ml THF) and diethylazodicarboxylate (4.3 ml, 27.5 mmol in 10 ml THF) at 0° C. The mixture was warmed to room temperature and stirred for 2 hours. The solvent was evaporated and the residue was purified by column chromatography on silica gel (ethyl acetate/hexane, 1:7) to afford the title compound (6.2 g, 87% yield).

$^1$H NMR (CDCl$_3$) δ 8.05 (m, 2H), 7.57 (m, 1H), 7.45 (m, 2H), 7.26 (m, 1H), 6.96 (m, 3H), 5.57 (m, 1H), 3.43 (m, 1H), 2.35 (m, 3H), 2.00 (m, 2H), 1.68 (m, 1H).

Step 5, trans-3-(fluorophenyl)-cyclopentan-1-ol

To a solution of the compound prepared in Step 4, above (6.10 g, 20 mmol), in MeOH (25 ml) and THF (25 ml), was added KOH (6 g, 0.11 mol) and water (1 ml). After stirring for about 2 hours, the reaction mixture was extracted with CH$_2$Cl$_2$ and washed with 1N aqueous HCl, saturated aqueous NaHCO$_3$ and brine, then was dried over MgSO$_4$ and concentrated. Purification by column chromatography on silica gel (ethyl acetate/hexane, 1:6) afforded the title compound (3.5 g, 97% yield).

$^1$H NMR (CDCl$_3$) δ 7.24 (m, 1H), 7.01–6.83 (m, 3H), 4.54 (m, 1H), 4.45 (br s, 1H), 3.40 (m, 1H), 2.31–2.04 (m, 3H), 1.86–1.57 (m, 3H).

Step 6, N-[cis-3-(3-fluorophenyl)cyclopentyl] hydroxylamine

To a solution of the compound prepared in Step 5, above (3.2 g, 17 mmol), PPh$_3$ (6.06 g, 22 mmol), and N,O-di-tert-butoxycarbonylhydroxylamine (4.5 g, 18 mmol) in THF (15 ml), cooled to −40° C., was added dropwise a solution of diethylazodicarboxylate (3.8 ml, 22 mmol) in THF (10 ml). The reaction mixture was warmed to room temperature overnight and the solvent removed under reduced pressure. Chromatography on silica gel (ethyl acetate/hexane, 1:9) gave 6.7 g of the crude N,O-di-tert-butoxycarbonyl-N-[cis-3-(3-fluorophenyl)cyclopentyl]hydroxylamine. To a stirred solution of the protected hydroxylamine obtained as above in CH$_2$Cl$_2$ (40 ml), cooled to 0° C., was slowly added trifluoroacetic acid (12.5 ml). The reaction mixture was allowed to warm to room temperature for 6 hours and then solvent was evaporated off. The resultant residue was covered with saturated aqueous NaHCO$_3$ (50 ml) and extracted with CH$_2$Cl$_2$ (2×100 ml). The combined extracts were washed with brine (50 ml) and dried over MgSO$_4$, and solvent was removed under reduced pressure. Chromatography on silica gel (ethyl acetate/hexane, 1:2) afforded the title compound (1.9 g, 64% yield) as a yellow solid.

$^1$H NMR (CDCl$_3$) δ 8.44 (br s, 2H), 7.22 (m, 1H), 6.93 (m, 3H), 3.76 (m, 1H), 3.02 (m 1H), 2.42 (m, 1H), 1.99 (m, 3H), 1.86–1.61 (m, 2H).

Step 7, N-[cis-3-(3-fluorophenyl)cyclopentyl]-N-hydroxyurea

To a stirred solution of the compound prepared in Step 6, above (2.4 g, 12 mmol), in THF (10 ml) was added trimethylsilylisocyanate (85%, 2.4 ml, 18 mmol) and the reaction mixture was stirred at room temperature for 1.5 hours. Methanol (10 ml) was added and 10 minutes later the solvent was removed under reduced pressure to afford a white solid. Recrystallization from IPE/hexane afforded the title compound (1.6 g, 57% yield) as a colorless solid, m.p. 104.2–105.7° C.

IR (KBr) v 3500, 2950, 2900, 1620, 1570, 1470, 1150, 880 cm$^{-1}$.

$^1$H NMR (DMSO-d$_6$) δ 9.10 (s, 1H), 7.32 (m, 1H), 7.04 (m, 3H), 6.29 (s, 2H), 4.67 (m, 1H), 3.00 (m, 1H), 2.12–1.58 (m, 6H).

Anal. Calc. for C$_{12}$H$_{15}$N$_2$O$_2$F: C, 60.49; H, 6.34; N, 11.76. Found: C, 60.45; H, 6.50; N, 11.72.

Example 101

N-hydroxy-N-[trans-3-(4-phenoxyphenyl)cyclopentyl]urea

Trans:cis=>20:1.

m.p. 130.9–131.6° C.

IR (KBr) v 3520, 3400, 3200, 1650, 1560, 1510, 1485, 1440, 1235 cm$^{-1}$.

$^1$H NMR (DMSO-d$_6$) δ 9.10 (s, 1H), 7.37 (t, J=7.9 Hz, 2H), 7.24 (d, J=8.4 Hz, 2H), 7.11 (t, J=7.3 Hz, 1H), 7.02–6.91 (m, 4H), 6.27 (s, 2H), 4.82–4.69 (m, 1H), 3.23–3.06 (m, 1H), 2.13–1.65 (m, 5H), 1.58–1.40 (m, 1H).

Example 102

N-[3-(4-fluorophenyl)cyclopentyl]methyl-N-hydroxyurea

Step 1, 3-(4-fluorophenyl)cyclopentanone

Hydrogenation of 3-(4-fluorophenyl)cyclopent-2-en-1-one was carried out according to the procedure of M. Kolobielski et al., *J. Am. Chem. Soc.*, 79, 5820 (1957).

$^1$H NMR (CDCl$_3$) δ 7.22 (m, 2H), 7.02 (m, 2H), 3.38 (m, 1H), 2.66 (dd, J=8.06 Hz, 1H), 2.52–2.23 (m, 4H), 1.95 (m, 1H).

Step 2, 3-(4-fluorophenyl)cyclopentanecarboxaldehyde

The title compound was prepared according to the procedure of G. L. Grunewald, *J. Med. Chem.*, 32, 478 (1989).

$^1$H NMR (CDCl$_3$) δ 9.70 (s, 1H), 7.19 (m, 2H), 6.98 (m, 2H), 2.98 (m, 2H), 2.29–1.59 (m, 6H).

Step 3, 3-(4-fluorophenyl)cyclopentylmethanol

A solution of the carboxaldehyde prepared in Step 2, above (2.8 g, 14 mmol), in MeOH (30 ml) was cooled to 0° C., and NaBH$_4$ (0.54 g, 14 mmol) was added slowly in solid form. The reaction mixture was warmed to room temperature, stirred for 30 minutes, and then quenched with ice cold water. The reaction mixture was extracted with ethyl acetate (3×20 ml) and the combined extracts were dried over MgSO$_4$. Volatiles were removed under reduced pressure and the residue was purified by column chromatography on silica gel (ethyl acetate/hexane, 1:7) to afford the title compound (2.6 g, 92% yield).

$^1$H NMR (CDCl$_3$) δ 7.18 (m, 2H), 6.96 (m, 2H), 3.60 (m, 2H), 3.05 (m, 1H), 2.30–1.55 (m, 8H).

Step 4, N-[3-(4-fluorophenyl)cyclopentyl]methyl-N-hydroxyurea

The title compound (after recrystallization from MeOH/hexane) was prepared from the product of Step 3, above, according to the procedure described in Example 100, m.p. 138.9–140° C.

IR (KBr) v 3500, 3350, 3200, 2860, 1640, 1570, 1510, 1470, 1160 cm$^{-1}$.

$^1$H NMR (DMSO-d$_6$) δ 9.21 (s, 1H), 7.27 (m, 2H), 7.08 (m, 2H), 6.20 (br s, 2H), 3.33 (m, 2H), 3.06 (m, 1H), 2.45 (m, 1H), 2.09–1.21 (m, 6H).

Anal. Calc. for C$_{13}$H$_{17}$N$_2$O$_2$F: C, 61.89; H, 6.79; N, 11.10. Found: C, 61.68; H, 6.95; N, 11.04.

Example 103

N-[trans-3-(4-chlorophenyl)cyclopentyl]-N-hydroxyurea m.p. 143.0–144.2° C.

IR (KBr) v 3500, 3200, 2950, 2850, 1660, 1580, 1440, 1180, 1100, 770 cm$^{-1}$.

$^1$H NMR (DMSO-d$_6$) δ 9.12 (s, 1H), 7.29 (m, 4H), 6.28 (br s, 2H), 4.72 (m, 1H), 3.14 (m, 1H), 1.95 (m, 5H), 1.72 (m, 1H).

Example 104

N-[cis-(3,4-difluorophenyl)cyclopentyl]-N-hydroxyurea m.p. 107.2–108.5° C.

IR (KBr) v 3490, 3200, 2950, 2850, 1660, 1570, 1520, 1450, 1370, 770 cm$^{-1}$.

$^1$H NMR (DMSO-d$_6$) δ 9.10 (s, 1H), 7.32 (m, 2H), 7.10 (m, 1H), 6.30 (br s, 2H), 4.67 (m, 1H), 2.97 (m, 1H), 1.83 (m, 6H).

Example 105

N-[cis-3-(2-fluorophenyl)cyclopentyl]-N-hydroxyurea m.p. 118.2–119.3° C.

IR (KBr) v 3500, 3200, 2950, 2870, 1660, 1640, 1580, 1490, 1450, 1220, 750 cm$^{-1}$.

$^1$H NMR (DMSO-d$_6$) δ 9.11 (s, 1H), 7.36 (m, 1H), 7.17 (m, 3H), 6.28 (br s, 2H), 4.66 (m, 1H), 3.20 (m, 1H), 1.84 (m, 6H).

Example 106

N-[trans-(3,4-difluorophenyl)cyclopentyl]-N-hydroxyurea m.p. 100.7–101.8° C.

IR (KBr) ν 3500, 3200, 2950, 2850, 1650, 1520, 1440 cm$^{-1}$.

$^1$H NMR (DMSO-d$_6$) δ 9.10 (s, 1H), 7.31 (m, 2H), 7.08 (m, 1H), 6.27 (br s, 2H), 4.74 (m, 1H), 3.13 (m, 1H), 1.86 (m, 5H), 1.48 (m, 1H).

Example 107

N-hydroxy-N-[trans-3-(4-fluoromethylphenyl)cyclopentyl]urea m.p. 135.1–136.3° C.

IR (KBr) ν 3500, 3450, 2950, 1640, 840 cm$^{-1}$.

$^1$H NMR (DMSO-d$_6$) δ 9.15 (s, 1H), 7.63 (d, J=8.06 Hz, 2H), 7.46 (d, J=8.06 Hz, 2H), 6.28 (br s, 2H), 4.75 (m, 1H), 3.27 (m, 1H), 1.91 (m, 5H), 1.52 (m, 1H).

Example 108

N-hydroxy-N-(trans-2-phenylcyclopentyl)urea m.p. 148.2–149.9° C.

IR (KBr) ν 3490, 3200, 1670, 1580, 1450, 1160, 790 cm$^{-1}$.

$^1$H NMR (DMSO-d$_6$) δ 9.07 (s, 1H), 7.26 (m, 4H), 7.16 (m, 1H), 6.18 (br s, 2H), 4.58 (m, 1H), 3.18 (m, 1H), 2.25 (m, 1H), 1.62 (m, 5H).

Example 109

N-[trans-3-(2-4-difluorophenyl)cyclopentyl]-N-hydroxyurea m.p. 113.0–114.1° C.

IR (KBr) ν 3500, 3200, 1620, 1570, 1420, 1140, 970 cm$^{-1}$.

$^1$H NMR (DMSO-d$_6$) δ 9.13 (s, 1H), 7.37 (m, 1H), 7.14 (m, 1H), 7.02 (m, 1H), 6.30 (br s, 2H), 4.74 (m, 1H), 3.32 (m, 1H), 2.04–1.50 (m, 6H).

Example 110

N-hydroxy-N-(cis-2-phenylcyclopentyl)urea m.p. 118.8–120.0° C.

IR (KBr) ν 3500, 3350, 3190, 1650, 1620, 1460, 800 cm$^{-1}$.

$^1$H NMR (DMSO-d$_6$) δ 8.75 (s, 1H), 7.29–7.08 (m, 5H), 5.72 (br s, 2H), 4.92 (m, 1H), 3.05 (m, 1H), 2.10–1.89 (m, 5H), 1.54 (m, 1H).

Example 111

N-hydroxy-N-[cis-3-(4-trifluoromethylphenyl)cyclopentyl]urea m.p. 124.2–125.5° C.

IR (KBr) ν 3490, 3200, 2990, 2910, 1660, 1570, 1440, 1320, 1120 cm$^{-1}$.

$^1$H NMR (DMSO-d$_6$) δ 9.13 (s, 1H), 7.49 (d, J=8.06 Hz, 2H), 7.48 (d, J=8.06 Hz, 2H), 6.29 (br s, 2H), 4.70 (m, 1H), 3.06 (m, 1H), 2.11–1.61 (m, 6H).

Example 112

N-[cis-3-(2,4-difluorophenyl)cyclopentyl]-N-hydroxyurea m.p. 125.2–126.0° C.

IR (KBr) ν 3490, 3350, 1610, 1590, 1510, 1470, 980 cm$^{-1}$.

$^1$H NMR (DMSO-d$_6$) δ 9.10 (s, 1H), 7.39 (m, 1H), 7.15 (m, 1H), 7.03 (m, 1H), 6.29 (br s, 2H), 4.67 (m, 1H), 3.14 (m, 1H), 2.06–1.61 (m, 6H).

Example 113

N-[cis-3-(4-fluorophenyl)cyclopentyl]-N-hydroxyurea m.p. 122.5–123.3° C.

IR (KBr) ν 3490, 3200, 2950, 2850, 1620, 1570, 1510, 1250, 930 cm$^{-1}$.

$^1$H NMR (DMSO-d$_6$) δ 9.09 (s, 1H), 7.28 (m, 2H), 7.09 (m, 2H), 6.28 (s, 2H), 4.67 (m, 1H), 2.93 (m, 1H), 2.09–1.55 (m, 6H).

Example 114

N-hydroxy-N-(cis-3-phenylcyclopentyl)urea

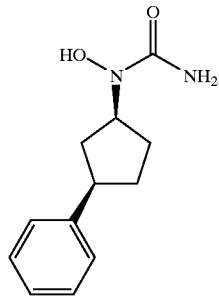

m.p. 132.0–134.3° C.

IR (KBr) ν 3470, 3200, 2870, 1620, 1570, 1470, 1150, 800 cm$^{-1}$.

$^1$H NMR (DMSO-d$_6$) δ 9.10 (s, 1H), 7.26 (m, 5H), 6.28 (s, 2H), 4.70 (s, 1H), 2.91 (m, 1H), 2.06–1.58 (m, 6H).

Example 115

N-[cis-3-(4-chlorophenyl)cyclopentyl]-N-hydroxyurea m.p. 143.0–144.3° C.

IR (KBr) ν 3500, 320, 2950, 1660, 1630, 1570, 1450, 830 cm$^{-1}$.

$^1$H NMR (DMSO-d$_6$) δ 9.10 (s, 1H), 7.31 (m, 4H), 6.29 (br s, 2H), 4.67 (m, 1H), 2.96 (m, 1H), 1.56–2.07 (m, 6H).

Example 116

N-hydroxy-N-(trans-3-phenylcyclopentyl)urea m.p. 122.4–123.6° C.

IR (KBr) ν 3500, 3350, 3200, 3000, 2850, 1610, 1570, 1500–1400, 800 cm$^{-1}$.

$^1$H NMR (DMSO-d$_6$) δ 9.11 (s, 1H), 7.3–7.15 (m, 5H), 6.28 (s, 2H), 4.74 (m, 1H), 3.14 (m, 1H), 2.11–1.46 (m, 6H).

Example 117

N-[trans-3-(2-fluorophenyl)cyclopentyl]-N-hydroxyurea m.p. 78.5–80.5° C.

IR (KBr) v 3500, 3300, 2950, 2850, 1650, 1560, 1490, 1220, 750 cm$^{-1}$.

$^1$H NMR (DMSO-d$_6$) δ 9.14 (s, 1H), 7.22 (m, 4H), 6.29 (br s, 2H), 4.74 (m, 1H), 3.46 (m, 1H), 1.79 (m, 6H).

Example 118

N-[trans-3-(4-fluorophenyl)cyclopentyl]-N-hydroxyurea m.p. 121.7–122.8° C.

IR (KBr) v 3490, 3350, 3200, 1610, 1580, 1510, 1240, 840 cm$^{-1}$.

$^1$H NMR (DMSO-d$_6$) δ 9.11 (s, 1H), 7.26 (m, 2H), 7.08 (m, 2H), 6.28 (br s, 2H), 4.74 (m, 1H), 3.14 (m, 1H), 1.87 (m, 5H), 1.47 (m, 1H).

Example 119

N-hydroxy-N-[cis-3-(3-methylphenyl)cyclopentyl]urea

Cis:trans=>20:1.

m.p. 112.0–113.0° C.

IR (KBr) v 3490, 3350, 3200, 2950, 1610, 1585, 1465, 1425 cm$^{-1}$.

$^1$H NMR (DMSO-d$_6$) δ 9.08 (s, 1H), 7.16 (t, J=7.3 Hz, 1H), 7.09–6.92 (m, 3H), 6.28 (s, 2H), 4.7304.59 (m, 1H), 2.94–2.83 (m, 1H), 2.27 (s, 3H), 2.07–1.55 (m, 6H).

Example 120

N-hydroxy-N-[trans-3-(3-methylphenyl)cyclopentyl]urea

Trans:cis=>20:1.

m.p. 109.9–110.8° C.

IR (KBr) v 3475, 3400, 3200, 2950, 2870, 1620, 1570, 1440 cm$^{-1}$.

$^1$H NMR (DMSO-d$_6$) δ 9.10 (s, 1H), 7.15 (t, J=7.3 Hz, 1H), 7.06–6.93 (m, 3H), 6.28 (s, 2H), 4.79–4.68 (m, 1H), 3.17–3.04 (m, 1H), 2.27 (s, 3H), 2.14–1.64 (m, 5H), 1.57–1.42 (m, 1H).

Example 121

N-hydroxy-N-[cis-3-(4-methylphenyl)cyclopentyl]urea

Cis:trans=>20:1.

m.p. 149.8–150.4° C.

IR (KBr) v 3470, 3250, 2980, 1660, 1575, 1520, 1420, 1140 cm$^{-1}$.

$^1$H NMR (DMSO-d$_6$) δ 9.07 (s, 1H), 7.15–7.06 (m, 4H), 6.25 (s, 2H), 4.72–4.59 (m,1H), 2.95–2.82 (m, 1H), 2.25 (s, 3H), 2.05–1.53 (m, 6H).

Example 122

N-hydroxy-N-[trans-3-(4-methylphenyl)cyclopentyl]urea

Trans:cis=>20:1.

m.p. 135.2–135.8° C.

IR (KBr) v 3500, 3340, 3200, 1660, 1580, 1460, 1440 cm$^{-1}$.

$^1$H NMR (DMSO-d$_6$) δ 9.10 (s, 1H), 7.16–7.03 (m, 4H), 6.27 (s, 2H), 4.80–4.65 (m, 1H), 3.18–3.02 (m, 1H), 2.25 (s, 3H), 2.10–1.61 (m, 5H), 1.55–1.37 (m, 1H).

Example 123

N-hydroxy-N-[3-(3-methoxyphenyl)cyclopentyl]urea

Cis:trans=9:1.

m.p.—(oil).

IR (Liquid Cell) v 3200, 3020, 2900, 2875, 1660, 1585, 1565, 1440, 1220, 1210 cm$^{-1}$.

$^1$H NMR (DMSO-d$_6$) δ 9.11 (s, 1H), 7.19 (t, J=7.7 Hz, 1H), 6.40–6.21 (m, 3H), 6.84 (s, 2H), 4.75–4.59 (m, 1H), 3.73 (s, 3H), 3.00–2.82 (m, 1H), 2.13–1.48 (m, 6H).

Example 124

N-hydroxy-N-[3-(3-methoxyphenyl)cyclopentyl]urea

Trans:cis=9:1.

m.p.—(oil).

IR (Liquid Cell) v 3025, 2800, 1670, 1560, 1520, 1480, 1430, 1220, 1210 cm$^{-1}$.

$^1$H NMR (DMSO-d$_6$) δ 9.10 (s, 1H), 7.18 (t, J=7.9 Hz, 1H), 6.86–6.68 (m, 3H), 6.28 (s, 2H), 4.81–4.67 (m, 1H), 3.37 (s, 3H), 3.19–3.04 (m, 1H), 2.10–1.63 (m, 5H), 1.58–1.40 (m, 1H).

Example 125

N-hydroxy-N-[cis-3-(4-methoxyphenyl)cyclopentyl]urea

Cis:trans=>20:1.

m.p. 139.4–140.3° C.

IR (KBr) v 3475, 3350, 3200, 1620, 1575, 1520, 1470, 1260 cm$^{-1}$.

$^1$H NMR (DMSO-d$_6$) δ 9.11 (s, 1H), 7.16 (d, J=8.4 Hz, 2H), 6.84 (d, J=8.4 Hz, 2H), 6.28 (s,2H), 4.73–4.59 (m, 1H), 3.71 (s, 3H), 2.95–2.82 (m, 1H), 2.05–1.56 (m,6H).

Example 126

N-hydroxy-N-[trans-3-(4-methoxyphenyl)cyclopentyl]urea

Trans:cis=>20:1.

m.p. 133.7–134.6° C.

IR (KBr) v 3475, 3350, 2950, 2880, 1610, 1585, 1515, 1460, 1445, 1250 cm$^{-1}$.

$^1$H NMR (DMSO-d$_6$) δ 9.08 (s, 1H), 7.13 (d, J=8.8 Hz, 2H), 6.83 (d, J=8.8 Hz, 2H), 6.27 (s, 2H), 4.80–4.64 (m, 1H), 3.71 (s, 3H), 3.17–3.02 (m, 1H), 2.08–1.62 (m, 5H), 1.55–1.36 (m, 1H).

Example 127

N-hydroxy-N-[cis-3-(3-phenoxyphenyl)cyclopentyl]urea

Cis:trans=20:1.

m.p. 103.0–103.6° C.

IR (KBr) v 3475, 3325, 3150, 2900, 1655, 1580, 1490, 1250, 1220, 1165 cm$^{-1}$.

$^1$H NMR (DMSO-d$_6$) δ 9.07 (s, 1H), 7.38 (dd, J=8.4, 7.3 Hz, 2H), 7.29 (t, J=8.1 Hz, 1H), 7.13 (t, J=7.3 Hz, 1H), 7.05–6.97 (m, 3H), 6.92 (d, J=1.8 Hz, 1H), 6.79 (dd, J=2.4, 7.9 Hz, 1H), 6.26 (s, 2H), 4.72–4.50 (m, 1H), 3.00–2.80 (m, 1H), 2.05–1.51 (m, 6H).

Example 128

N-hydroxy-N-[trans-3-(3-(3-phenoxyphenyl)cyclopentyl]urea

Trans:cis=>20:1.

m.p.—(oil).

IR (Liquid Cell) v 3700, 3550, 3420, 3020, 1670, 1650, 1580, 1560, 1490, 1440, 1220 cm$^{-1}$.

$^1$H NMR (DMSO-d$_6$) δ 9.11 (s, 1H), 7.38 (t, J=7.3 Hz, 2H), 7.28 (t, J=7.7 Hz, 1H), 7.12 (t, J=7.1 Hz, 1H), 6.99 (d, J=7.0 Hz, 3H), 6.88 (s, 1H), 6.77 (d, 7.7 Hz, 1 H) 6.29 (s, 2H), 4.80–4.65 (m, 1H), 3.21–3.04 (m, 1H), 2.12–1.61 (m, 5H), 1.58–1.38 (m, 1H).

Example 129

N-hydroxy-N-[cis-3-(4-phenoxyphenyl)cyclopentyl]urea

Cis:trans=>20:1.

m.p. 139.0–139.8° C.

IR (KBr) v 3475, 3330, 3200, 2960, 2880, 1620 1575, 1510, 1490, 1260 cm$^{-1}$.

$^1$H NMR (DMSO-d$_6$) δ 9.09 (s, 1H), 7.37 (t, J=7.5 Hz, 2H), 7.27 (d, J=8.1 Hz, 2H), 7.10 (t, J=7.7 Hz, 1H), 6.95 (t, J=8.1 Hz, 4H), 6.27 (s, 2H), 4.72–4.60 (m, 1H), 3.01–2.87 (m, 1H), 2.09–1.54 (m, 6H).

Example 130

N-[(1-benzocyclobutyl)methyl]-N-hydroxyurea m.p. 119–121° C.

IR (nujol) v 3450, 3190, 1670, 1575, 1340, 1150, 765, 750 cm$^{-1}$.

$^1$H NMR (CDCl$_3$) δ 9.15 (s, 1H), 7.11 (m, 4H), 5.50 (s, 2H), 3.83 (s, 2H), 3.83 (m, 1H), 3.33 (m, 1H), 2.98 (d, J=4.3 Hz, 1H).

What is claimed is:

1. A process for preparing a compound of the formula

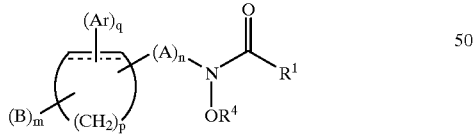

wherein R$^1$ is hydrogen, C1 to C4 alkyl, C2 to C4 alkenyl, alkylthioalkyl, alkoxyalkyl or NR$^2$R$^3$;

R$^2$ and R$^3$ are each independently hydrogen, C1 to C4 alkyl, hydroxy, aryl, or aryl substituted with one or more substituents selected from the group consisting of halo, nitro, cyano, C1 to C12 alkyl, C1 to C12 alkoxy, C1 to C12 halosubstituted alkyl, C1 to C12 hydroxysubstituted alkyl, C1 to C12 alkoxycarbonyl, aminocarbonyl, C1 to C12 alkylaminocarbonyl, di C1 to C12 alkylaminocarbonyl and C1 to C12 alkylsulfonyl, provided that R$^2$ and R$^3$ are not both hydroxy;

R$^4$ is hydrogen, a pharmaceutically acceptable cation, aroyl or C1 to C6 alkoyl;

A is C1 to C6 alkylene or C2 to C6 alkenylene;

each B is independently halo, nitro, cyano, —SH, hydroxy, C1 to C6 alkyl, C1 to C6 alkoxy, C1 to C6 halosubstituted alkyl, C1 to C6 thioalkyl, C2 to C6 alkenyl, C1 to C12 aminocarbonyl, C1 to C6 alkylaminocarbonyl, di C1 to C6 alkylaminocarbonyl or C2 to C12 alkoxyalkyl;

each Ar is independently phenyl, naphthyl, pyridyl, quinolyl, thienyl, furyl, phenoxyphenyl or any of the foregoing substituted with one or more substituents selected from the group consisting of hydroxy, halo, nitro, cyano, C1 to C12 alkyl, C1 to C12 alkoxy, C1 to C12 halosubstituted alkyl, C1 to C12 hydroxysubstituted alkyl, C1 to C12 alkylamino, di C1 to C12 alkylamino, C1 to C12 alkoxycarbonyl, aminocarbonyl, C1 to C12 alkylaminocarbonyl, di C1 to C12 alkylaminocarbonyl and C1 to C12 alkylsulfonyl;

Ar and B, together with the carbon atoms to which they are attached may form a ring;

n is 0 or 1;

m is 0 to 3;

p is 1 to 6;

q is 1 or 2; and

. . . represents an optional bond, comprising:

(I) selectively hydrolyzing a compound having the formula

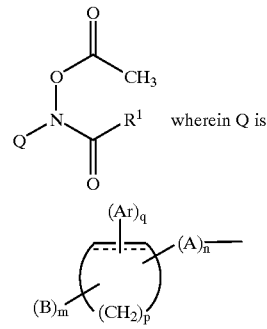 wherein Q is with a base selected from ammonium hydroxide, sodium hydroxide, potassium hydroxide and lithium hydroxide in a solvent system under conditions including a reaction temperature of between −10° C. and ambient temperature;

(II) reaction of a compound having the formula

wherein Q is as defined above, with trimethylsilyl isocyanate in a reaction-inert solvent under conditions including a reaction temperature of between ambient and reflux temperature.

2. A process according to claim 1 wherein:

when process (I) is used, said solvent system is selected from one or more of water, methanol, ethanol, propanol and tetrahydrofuran;

when process (II) is used, said reaction-inert solvent is selected from tetrahydrofuran, dioxane, methylene chloride and benzene; and when process (III) is used, said reaction-inert solvent is selected from benzene and toluene.

3. A process according to claim 2 further comprising the step of isolating said prepared compound.

4. A process according to claim 3 wherein $R^4$ is hydrogen.

5. A process according to claim 4 wherein:
$R^1$ is amino;
n is 0;
m is 0;
p is 2 or 3;
q is 1;
Ar is phenyl, fluorophenyl or phenoxyphenyl; and
. . . represents no bond.

6. A compound of the formula

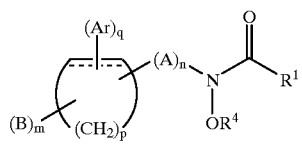

wherein $R^1$ is hydrogen, C1 to C4 alkyl, C2 to C4 alkenyl, alkylthioalkyl, alkoxyalkyl or $NR^2R^3$;
$R^2$ and $R^3$ are each independently hydrogen, C1 to C4 alkyl, hydroxy, aryl, or aryl substituted with one or more substituents selected from the group consisting of halo, nitro, cyano, C1 to C12 alkyl, C1 to C12 alkoxy, C1 to C12 halosubstituted alkyl, C1 to C12 hydroxysubstituted alkyl, C1 to C12 alkoxycarbonyl, aminocarbonyl, C1 to C12 alkylaminocarbonyl, di C1 to C12 alkylaminocarbonyl and C1 to C12 alkylsulfonyl, provided that $R^2$ $R^3$ are not both hydroxy;
$R^4$ is hydrogen, a pharmaceutically acceptable cation, aroyl or C1 to C6 alkoyl;
A is C1 to C6 alkylene or C2 to C6 alkenylene;
each B is independently halo, nitro, cyano, —SH, hydroxy, C1 to C6 alkyl, C1 to C6 alkoxy, C1 to C6 halosubstituted alkyl, C1 to C6 thioalkyl, C2 to C6 alkenyl, C1 to C12 aminocarbonyl, C1 to C6 alkylaminocarbonyl, di C1 to C6 alkylaminocarbonyl or C2 to C12 alkoxyalkyl;
each Ar is independently phenyl, naphthyl, pyridyl, quinolyl, thienyl, furyl, phenoxyphenyl or any of the foregoing substituted with one or more substituents selected from the group consisting of hydroxy, halo, nitro, cyano, C1 to C12 alkyl, C1 to C12 alkoxy, C1 to C12 halosubstituted alkyl, C1 to C12 hydroxysubstituted alkyl, C1 to C12 alkylamino, di C1 to C12 alkylamino, C1 to C12 alkoxycarbonyl, aminocarbonyl, C1 to C12 alkylaminocarbonyl, di C1 to C12 alkylaminocarbonyl and C1 to C12 alkylsulfonyl;
Ar and B, together with the carbon atoms to which they are attached, may form a ring;
n is 0 or 1;
m is 0 to 3;
p is 1 to 6;
q is 1 or 2; and
. . . represents an optional bond.

7. A compound according to claim 6 wherein $R^4$ is hydrogen.

8. A compound according to claim 6 and 7 wherein p is 4.

9. A compound according to claim 6 or 7 wherein p is 3.

10. A compound according to claim 6 or 7 wherein p is 2.

11. A compound according to claim 6 or 7 wherein p is 1.

12. A compound according to claim 11 wherein Ar and B, together with the carbon atoms to which they are attached, form a ring.

13. A compound according to claim 8 wherein $R^1$ is C1 to C4 alkyl or $NR^2R^3$.

14. A compound according to claim 13 wherein:
$R^1$ is $NR^2R^3$.
$R^2$ and $R^3$ are each hydrogen; and
Ar is phenyl.

15. A compound according to claim 13 wherein:
$R^1$ is methyl; and
Ar is phenoxyphenyl.

16. A compound according to claim 9 wherein $R^1$ is C1 to C4 alkyl or $NR^2R^3$.

17. A compound according to claim 16 wherein:
$R^1$ is $NR^2R^3$;
$R^2$ is $R^3$ are each hydrogen; and
Ar is phenyl.

18. A compound according to claim 10 wherein $R^1$ is C1 to C4 alkyl or $NR^2R^3$.

19. A compound according to claim 18 wherein:
$R^1$ is $NR^2R^3$;
$R^2$ and $R^3$ are each hydrogen; and
Ar is phenyl.

20. A compound according to claim 11 wherein $R^1$ is C1 to C4 alkyl or $NR^2R^3$.

21. A compound according to claim 20 wherein:
$R^1$ is $NR^2R^3$;
$R^2$ and $R^3$ are each hydrogen; and Ar is phenyl or phenoxyphenyl.

22. A compound according to claim 20 wherein $R^1$ is methyl.

23. A compound according to claim 6 wherein B is halo.

24. A compound according to claim 23 wherein:
B is fluorine; and
m is 1 or 2.

25. A compound according to claim 12 wherein:
$R^1$ is $NH_2$; and
Ar is phenyl.

26. A compound according to claim 21 which is N-hydroxy-N-[(trans-2-phenyl-1-cyclopropyl)methyl]urea.

27. A compound according to claim 7 wherein:
$R^1$ is $NH_2$;
Ar is phenyl, fluorophenyl or phenoxyphenyl;
m is 0;
n is 0;
p is 2 or 3;
q is 1; and
. . . represents no bond.

28. A compound according to claim 27 which is N-[cis-3-(4-fluorophenyl)cyclobutyl]-N-hydroxyurea, N-hydroxy-N-[cis-3-(3-phenoxyphenyl)cyclobutyl]urea or N-hydroxy-N-(cis-3-phenylcyclopentyl)urea.

29. A method of treating allergy or inflammatory conditions in a mammal comprising administering to said mammal a lipoxygenase-inhibiting amount of compound according to claim 6 or a pharmaceutically acceptable salt thereof.

* * * * *